(12) United States Patent
Kriesel et al.

(10) Patent No.: US 11,225,358 B2
(45) Date of Patent: *Jan. 18, 2022

(54) IMMOBILIZING FLEXIBLE STOWAGE CONTAINERS

(71) Applicant: Tak Logic, LLC, Ettrick, WI (US)

(72) Inventors: Matthew Wayne Kriesel, Melrose, WI (US); Troy Bradley Goodenough, Mindoro, WI (US)

(73) Assignee: Tak Logic, LLC, Ettrick, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/678,917

(22) Filed: Nov. 8, 2019

(65) Prior Publication Data

US 2021/0086947 A1  Mar. 25, 2021

Related U.S. Application Data

(63) Continuation-in-part of application No. 15/731,815, filed on Aug. 7, 2017, now Pat. No. 11,124,596, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.

| | | |
|---|---|---|
| *B65D 25/04* | (2006.01) | |
| *B65D 33/06* | (2006.01) | |
| *B05D 1/02* | (2006.01) | |
| *A01K 97/06* | (2006.01) | |
| *A61B 50/33* | (2016.01) | |
| *B32B 37/12* | (2006.01) | |
| *C09D 175/08* | (2006.01) | |
| *C08K 5/1515* | (2006.01) | |
| *C08G 18/22* | (2006.01) | |
| *C09J 175/08* | (2006.01) | |
| *C08G 18/76* | (2006.01) | |
| *C09J 191/00* | (2006.01) | |
| *C08G 59/16* | (2006.01) | |
| *C09J 4/00* | (2006.01) | |
| *C08G 18/48* | (2006.01) | |
| *A61B 50/30* | (2016.01) | |
| *A61B 50/00* | (2016.01) | |
| *C08G 18/10* | (2006.01) | |
| *C08G 18/36* | (2006.01) | |
| *A45C 7/00* | (2006.01) | |
| *C08K 5/00* | (2006.01) | |

(52) U.S. Cl.
CPC .............. *B65D 25/04* (2013.01); *A01K 97/06* (2013.01); *A61B 50/33* (2016.02); *B05D 1/02* (2013.01); *B32B 37/12* (2013.01); *B65D 33/06* (2013.01); *C08G 18/227* (2013.01); *C08G 18/4812* (2013.01); *C08G 18/7671* (2013.01); *C08G 59/1472* (2013.01); *C08K 5/1515* (2013.01); *C09D 175/08* (2013.01); *C09J 4/00* (2013.01); *C09J 175/08* (2013.01); *C09J 191/00* (2013.01); *A45C 2007/0004* (2013.01); *A61B 2050/002* (2016.02); *A61B 2050/3008* (2016.02); *C08G 18/10* (2013.01); *C08G 18/36* (2013.01); *C08G 18/4825* (2013.01); *C08G 18/4829* (2013.01); *C08G 2390/40* (2013.01); *C08K 5/0016* (2013.01)

(58) Field of Classification Search
CPC ........ B65D 25/04; B65D 33/06; A61B 50/33; A61B 2050/002; A61B 2050/2008; A61B 2050/3008; A01K 97/06; B05D 1/02; C08G 18/10; C08G 18/36; C08G 18/4829; C08G 18/4825; C08G 2390/40; C08G 18/227; C08G 18/4812; C08G 18/7671; C08G 59/1472; A45C 2007/0004; B32B 37/00; B32B 37/12; C09J 191/00; C09J 175/08; C09J 4/00; C08K 5/0016; C08K 5/1515; C09D 175/08

See application file for complete search history.

(56) References Cited

U.S. PATENT DOCUMENTS

| | | | |
|---|---|---|---|
| 3,507,071 A | 4/1970 | Bryson | |
| 5,677,413 A | 10/1997 | Barksby et al. | |
| 5,864,001 A | 1/1999 | Masse et al. | |
| 6,588,511 B1 | 7/2003 | Kriesel et al. | |
| 6,673,409 B1 | 1/2004 | Wheatley | |
| 6,896,065 B2 | 5/2005 | Kriesel et al. | |
| 7,041,719 B2 * | 5/2006 | Kriesel | ..................... A01L 7/02 524/114 |
| 7,125,602 B2 | 10/2006 | Wheatley | |
| 7,252,867 B2 | 8/2007 | Wheatley | |
| 7,910,188 B2 | 3/2011 | Wheatley | |
| 7,923,088 B2 | 4/2011 | Wheatley | |
| 8,110,269 B2 | 2/2012 | Wheatley | |
| 8,110,270 B2 | 2/2012 | Wheatley | |
| 8,302,213 B2 | 11/2012 | Kriesel | |
| 9,974,342 B1 * | 5/2018 | Kriesel | .............. A41D 13/0512 |
| D880,950 S | 4/2020 | Kriesel et al. | |
| 10,681,830 B1 | 6/2020 | Goodenough | |
| 10,717,582 B1 | 7/2020 | Goodenough | |

(Continued)

*Primary Examiner* — Rabon A Sergent
(74) *Attorney, Agent, or Firm* — Bryan R. Rosiejka; M. Paul Hendrickson

(57) ABSTRACT

A unique flexible container combination comprises a viscoelastomeric thermoset overlay disposed upon a flexible supportive base. Desirably, the viscoelastomeric thermoset overlay possesses exceptional adhesive, cohesive and releasability properties. In some embodiments, the flexible container combination can also exhibit antipathogenic, cleansability and/or reusability properties. The flexible container combination can maintain an adhered stowable item in an immobilized position until intentionally removed therefrom by a user. In some embodiments, the flexible container combination can be folded or rolled into a rolled-up configuration.

34 Claims, 8 Drawing Sheets

(56) References Cited

U.S. PATENT DOCUMENTS

| | | | |
|---|---|---|---|
| 10,807,767 B1 * | 10/2020 | Kriesel | .............. C08G 59/1472 |
| D902,584 S | 11/2020 | Kriesel et al. | |
| 10,914,087 B1 | 2/2021 | Kriesel et al. | |
| 2004/0191446 A1 | 9/2004 | Kriesel | |
| 2004/0200623 A1 | 10/2004 | Kriesel | |
| 2006/0272367 A1 | 12/2006 | Kriesel | |
| 2006/0287147 A1 | 12/2006 | Kriesel | |
| 2008/0005929 A1 | 1/2008 | Hardy et al. | |
| 2008/0026658 A1 | 1/2008 | Kriesel | |
| 2008/0250729 A1 | 10/2008 | Kriesel | |
| 2009/0042676 A1 | 2/2009 | Kriesel | |
| 2010/0170139 A1 | 7/2010 | Zhou | |
| 2012/0222457 A1 | 9/2012 | Kriesel et al. | |
| 2015/0053583 A1 | 2/2015 | McCormick et al. | |

* cited by examiner

IMMOBILIZING FLEXIBLE STOWAGE CONTAINERS

CROSS-REFERENCE TO RELATED APPLICATION

This application is a Continuation-In-Part of, and claims priority to, U.S. Nonprovisional application Ser. No. 15/731,815 filed Aug. 7, 2017, which is a Continuation-In-Part of U.S. Nonprovisional application Ser. No. 14/999,722 filed Jun. 20, 2016, which is a Nonprovisional Application of U.S. Provisional Application No. 62/231,004 filed Jun. 22, 2015, all of which applications are incorporated herein by reference in their entirety.

FIELD OF INVENTION

The present invention relates to flexible containers, and more particularly to flexible containers equipped to immobilize stowed items from movement and methods thereof.

BACKGROUND

Throughout time, flexible vessels have been used as convenient stowage containers for a host of items. Flexible stowage containers are often provided in a bag form, and can optionally be fitted with carrying handles. Certain other flexible stowage containers are provided in a roll-up or hanging bag form, and are typically fitted with straps or strings to secure such containers in a rolled-up configuration. Such flexible containers are often equipped with compartments or divisions (often referred to as "pockets") sized to fit the dimensions and shape of a specific stowed item. Such pocketed flexible stowage containers are typically only useful for the specific stowable items for which the flexible stowage container was designed. An advantage of such roll-up containers resides in their compact stowing size when in a roll-up configuration. Exemplary roll-up containers include roll-up dump pouches, such as hunting and fishing roll-up bags and bag containers, tool bags, mini first aid kits, kitchenware holders (e.g., flatware, knives, silverware, etc.), hanging roll-up bags (e.g., for cosmetics, toiletries, jewelry, etc.), roll-up medical and EMT bags, military roll-up bags, hanging sales display containers, roll-up transporting containers, and the like. Often such flexible containers are fabricated with clear plastic pockets designed to visibly reveal the particular stowed item. Exemplary thereof are roll-up wrench holders fitted with transparent plastic pockets sized to match a particular wrench size. Unfortunately, under common usage, the compartmentalized sections are prone to deterioration and thus lose their functionality to effectively restrain the stowed items in proper order.

There exists a need for a flexible container which can more effectively immobilize stowed items while also retaining substantially all of the desirable flexible attributes of a conventional flexible stowage container. Further benefits would be achieved if it were possible to immobilize a stowable item without necessitating a specially designed restraint element for each particular item desired to be stowed therein. Flexible containers equipped to immobilize a vast array of stowable items irrespective of item size, shape, and weight would also represent a significant advance within the flexible container art. Further advantages would be accomplished if such a flexible container provided antipathogenic properties, washable attributes and/or possessed virtually unlimited reuse. It would also be of great advantage to provide a rolled-up flexible container which would not require securing means (e.g., strings, straps, etc.) to secure and maintain the container in a rolled-up configuration.

There also exists a need for a flexible container which can more effectively immobilize stowed items while also retaining substantially all of the desirable flexible attributes of a conventional flexible stowage container, and which additionally is transparent such that the contents within the container can be viewed without opening the container. Such transparent flexible containers would be useful in venues such as airports, athletic arenas, schools, etc. Further advantages would be accomplished if such transparent flexible containers provided antipathogenic properties, washable attributes and/or possessed virtually unlimited reuse. It would also be of great advantage to provide such transparent rolled-up flexible containers which would not require securing means (e.g., strings, straps, etc.) to secure and maintain the container in a rolled-up configuration.

It is evident that there clearly exists a long-standing need for a more effective flexible stowing container, especially within the field of roll-up or hanging types of flexible containers. Definitive advantages would be accomplished if it were possible to eliminate the need for tailor-made retaining pockets specifically adapted to retain only one specific item. Significant advantages would also be achieved if there existed a roll-up or hanging container having a universal capacity to restrain virtually any stowed item irrespective of its dimensions, weight or shape. Additional advantages would arise if the restraining system did not require tying strings or straps to maintain the container in a rolled-up form. Further advantages would arise if the restraining system would cohesively release the stowed item without leaving any unwanted residue upon the released item. Additional advantages would arise if the restraining system could be repeatedly reused without deterioration in restraining efficacy coupled with an ability to fully restore its restraining capacity by simple washing. Even further advantages over existing roll-up and hanging containers would be achieved if the containers possessed viscoelastomeric, adhesive and/or antipathogenic properties.

SUMMARY

In response, the invention of the present disclosure solves one or more of the problems and/or needs discussed above. More particularly, one or more of the aforementioned desired advantages, as well as other unexpected advantages, can be achieved by replacing the current pocket restraining systems of flexible roll-up or hanging containers with an antipathogenic, viscoelastomeric, cohesive and releasable adhesive thermoset polymer overlay which tenaciously adhesively restrains stowed items until needed. The overlay possesses cohesive release properties, which upon a sufficient opposing force, releases an adhered item from the overlay, desirably leaving substantially no polymeric residue on the item. Since the overlay can possess antipathogenic properties, the overlay can effectively alleviate the creation of an environment conducive to microbial growth. In addition, the overlay can help to secure and maintain the flexible container in a rolled-up configuration, without the need for a retaining member (e.g., straps, strings, hook-and-loop, etc.). The adhesive characteristics of the overlay may be tailored to adhesively suit a particular stowed item for which the flexible roll-up or hanging container is designed, or it may be tailored to adhesively suit a multiplicity of different items. Difficult to store small items (e.g., screws, nuts, coins, etc.) may easily be stored and retrieved in a readily accessible form with such flexible containers equipped with the overlay.

In some aspects, a flexible container combination comprises a flexible supportive base having a front side and a back side, and an adhesive and cohesive viscoelastomeric thermoset overlay disposed upon the front side of the flexible supportive base. In other aspects, the flexible container combination can be in the form of a roll-up container. In further aspects of such embodiments, an overall attachment force of the viscoelastomeric thermoset overlay to the front side of the flexible supportive base is greater than an adhesive force of the viscoelastomeric thermoset overlay to the back side of the flexible supportive base. In other aspects, the flexible container combination can be in the form of a bag. In still other aspects, the flexible container combination can be in the form of a hanging container. In yet other aspects, at least one of the viscoelastomeric thermoset overlay or flexible supportive base is transparent.

In some aspects, the viscoelastomeric thermoset overlay can have a thickness of about 0.5 mm to about 10 mm. In other aspects, the front side of the flexible supportive base can be at least partially impregnated with the viscoelastomeric thermoset overlay, and the back side of the flexible supportive base can be substantially free of the viscoelastomeric thermoset overlay.

In some aspects, the viscoelastomeric thermoset overlay comprises:
  a) about 1 wt % to about 10 wt % isocyanate prepolymer,
  b) about 35 wt % to about 55 wt % polyols comprising straight chain linking diols and cross-linking triols,
  c) about 10 wt % to about 50 wt % epoxidized triglyceride plasticizer, and
  d) about 0 wt % to about 40 wt % ester plasticizer.

In further aspects of such embodiments, the diols and triols each have repetitive ether groupings. In still further aspects of such embodiments, the viscoelastomeric thermoset overlay further comprises a diol to triol weight ratio of about 3:1 to about 1:3. In other aspects, the epoxidized triglyceride plasticizer and the ester plasticizer are uniformly dispersed throughout the viscoelastomeric thermoset overlay.

In some aspects, the viscoelastomeric thermoset overlay has been bonded to the flexible supportive base via in situ curing. In other aspects, the viscoelastomeric thermoset overlay has been prefabricated and adhesively applied to the flexible supportive base.

In some aspects, the viscoelastomeric thermoset overlay further comprises an epoxidized triglyceride plasticizer to ester plasticizer weight ratio of about 1:0 to about 6:1.

In some aspects, the ester plasticizer is selected from the group consisting of sebacates, dipates, glutarates, dibenzoates, phthalates, terephthalates, azelates, and combinations thereof. In other aspects, the ester plasticizer has a molecular weight of less than about 750. In still other aspects, the ester plasticizer has a dipole moment of at least about 1.5 D. In yet other aspects, the ester plasticizer comprises dibutyl sebacate in an amount of about 2 wt % to about 20 wt %. In still other aspects, the flexible container combination is transparent.

In some aspects, the viscoelastomeric thermoset overlay comprises:
  a) about 3 wt % to about 8 wt % diisocyanate prepolymer,
  b) about 10 wt % to about 35 wt % polyether diol as the straight chain linking diols,
  c) about 25 wt % to about 35 wt % polyether triol as the cross-linking triols,
  d) about 25 wt % to about 45 wt % epoxidized vegetable oil plasticizer, and
  e) about 0 wt % to about 40 wt % ester plasticizer.

In other aspects, the viscoelastomeric thermoset overlay further comprises a polyether diol to polyether triol weight ratio of about 3:1 to about 1:3. In still other aspects, the polyether diol and the polyether triol each comprise a polyoxyalkylene grouping selected from the group consisting of polyoxyethylene and polyoxypropylene. In further aspects of such embodiments, the polyether diol and the polyether triol each have a molecular weight of about 2,000 to about 10,000.

In some aspects, the viscoelastomeric thermoset overlay further comprises a sufficient polyether diol to polyether triol weight ratio and an epoxidized triglyceride plasticizer to ester plasticizer weight ratio to provide a sufficient adhesiveness for retaining an item disposed thereon against displacement via gravity, and further to provide a sufficient cohesiveness to retain structural integrity of the viscoelastomeric thermoset overlay upon removal of the item via a separation force applied by a user.

In some aspects, the viscoelastomeric thermoset overlay comprises:
  a) about 4 wt % to about 7 wt % diisocyanate prepolymer,
  b) about 10 wt % to about 20 wt % polyether diol having a molecular weight of about 2,000 to about 6,000,
  c) about 25 wt % to about 35 wt % polyether triol having a molecular weight of about 3,000 to about 7,000,
  d) about 25 wt % to about 45 wt % percent epoxidized soybean oil plasticizer, and
  e) about 0 wt % to about 40 wt % ester plasticizer having a molecular weight of less than about 750.

In further aspects of such embodiments, the viscoelastomeric thermoset overlay further comprises a polyether diol to polyether triol weight ratio of about 13:7 to about 7:13. In still further aspects of such embodiments, the viscoelastomeric thermoset overlay further comprises an epoxidized soy bean oil plasticizer to ester plasticizer weight ratio of about 1:0 to about 6:1. In yet further aspects of such embodiments, a reaction to form the viscoelastomeric thermoset overlay is carried out in the presence of a catalytic amount of a catalyst.

In some aspects, a flexible container combination comprises:
  a) a flexible supportive base having a front side and a back side, and
  b) an adhesive and cohesive viscoelastomeric thermoset overlay disposed upon the front side of the flexible supportive base,
where the viscoelastomeric thermoset overlay comprises a sufficient adhesive attraction to immobilize a stowed item placed in adhesive contact with the viscoelastomeric thermoset overlay, and where the viscoelastomeric thermoset overlay further comprises a sufficient cohesive releasability to detach the stowed item upon an application of a removing force sufficient to overcome the adhesive attraction. In other aspects of such embodiments, the flexible container combination is transparent.

In some aspects, a method for preparing a flexible container combination comprises:
  a) providing a flexible supportive base having a front side and a back side, wherein the flexible supportive base is of a sufficient size and structural integrity to support a desired stowable item, and b) overlaying the front side of the flexible supportive base with a thermoset viscoelastomeric reaction product to form a viscoelastomeric thermoset overlay disposed thereupon, where the viscoelastomeric thermoset overlay is bonded to the flexible supportive base by a thermoset bonding of the thermoset viscoelastomeric reaction product to the front side of the flexible supportive base or by an adhesive bonding of the viscoelastomeric thermoset overlay to the front side of the flexible supportive base. In further aspects of such embodiments, the viscoelastomeric thermoset overlay possesses adhesive, cohesive and releasability properties sufficient to retain a desired stowable item at a stabilized stowable position to form a stowed item, and to release the stowed item by application of a detachment force sufficient to overcome an adhesive attraction between the stowed item and the viscoelastomeric thermoset overlay to form a removed item. In still further aspects of such embodiments, the removed item exhibits no more than a nominal amount of a polymeric residue from the viscoelastomeric thermoset overlay. In some aspects, the flexible container combination is in the form of a roll up container. In other aspects, the flexible container combination is in the form of a bag container. In still other aspects, the flexible container combination is in the form of a hanging container.

In some aspects, the overlaying step of the method comprises disposing a reaction media which forms the thermoset viscoelastomeric reaction product onto the front side of the flexible supportive base and then curing the reaction media in situ. In other aspects, the overlaying step of the method comprises adhesively disposing a cured layer of the thermoset viscoelastomeric reaction product upon the front side of the flexible supportive base. In some aspects of the method, the viscoelastomeric thermoset overlay has a thickness of about 0.5 mm to about 10 mm. In other aspects of the method, at least one of the viscoelastomeric thermoset overlay or flexible supportive base is transparent.

In some aspects of the method, the viscoelastomeric thermoset overlay is derived from a thermosetting of a reaction media comprising:
  a) about 1 wt % to about 10 wt % diisocyanate prepolymer,
  b) about 35 wt % to about 55 wt % polyols comprising straight chain linking diols and cross-linking triols, and
  c) about 10 wt % to about 55 wt % plasticizer comprising about 10 wt % to about 50 wt % epoxidized triglyceride plasticizer and about 0 wt % to about 40 wt % ester plasticizer, where the diols and triols each have repetitive ether groupings, and where the reaction media further comprises a diol to triol weight ratio of about 3:1 to about 1:3. In other aspects of the method, the reaction media further comprises an epoxidized triglyceride plasticizer to ester plasticizer weight ratio of about 1:0 to about 6:1. In still other aspects of the method, the ester plasticizer has a molecular weight of less than about 750. In yet other aspects of the method, the ester plasticizer has a dipole moment of at least about 1.5 D. In still other aspects of the method, the ester plasticizer is selected from the group consisting of sebacates, dipates, glutarates, dibenzoates, phthalates, terephthalates, azelates, and combinations thereof.

In some aspects of the method, the reaction media comprises:
  a) about 3 wt % to about 8 wt % diisocyanate prepolymer,
  b) about 10 wt % to about 35 wt % polyether diol as the straight chain linking diol,
  c) about 25 wt % to about 35 wt % polyether triol as the cross-linking triol, and
  d) about 20 wt % to about 50 wt % plasticizer comprising about 25 wt % to about 45 wt % epoxidized vegetable oil plasticizer and about 0 wt % to about 40 wt % dibutyl sebacate plasticizer, where the polyether diol and the polyether triol each have a molecular weight ranging from about 2,000 to about 10,000. In further aspects of such embodiments, the reaction media further comprises a polyether diol to polyether triol weight ratio of about 13:7 to about 7:13. In still further aspects of such embodiments, the plasticizer is uniformly and cohesively dispersed throughout the reaction media. In yet further aspects of such embodiments, the amount of plasticizer within the reaction media is sufficient to provide a viscoelastomeric thermoset overlay possessing sufficient adhesiveness to stabilize the stowed item from unintentional displacement. In still further aspects of such embodiments, the amount of plasticizer within the reaction media is sufficient to provide a viscoelastomeric thermoset overlay possessing sufficient cohesiveness to prevent degradation of the viscoelastomeric thermoset overlay upon application of a detachment force to the stowed item. In other aspects of the method, the polyether diol and the polyether triol each comprise a polyoxyalkylene grouping selected from the group consisting of polyoxyethylene and polyoxypropylene.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5, and fractions thereof.

BRIEF DESCRIPTION OF THE FIGURES

The foregoing and other features, aspects and advantages of the present invention will become better understood with regard to the following description, appended claims and accompanying drawings where:

Figure 1A:
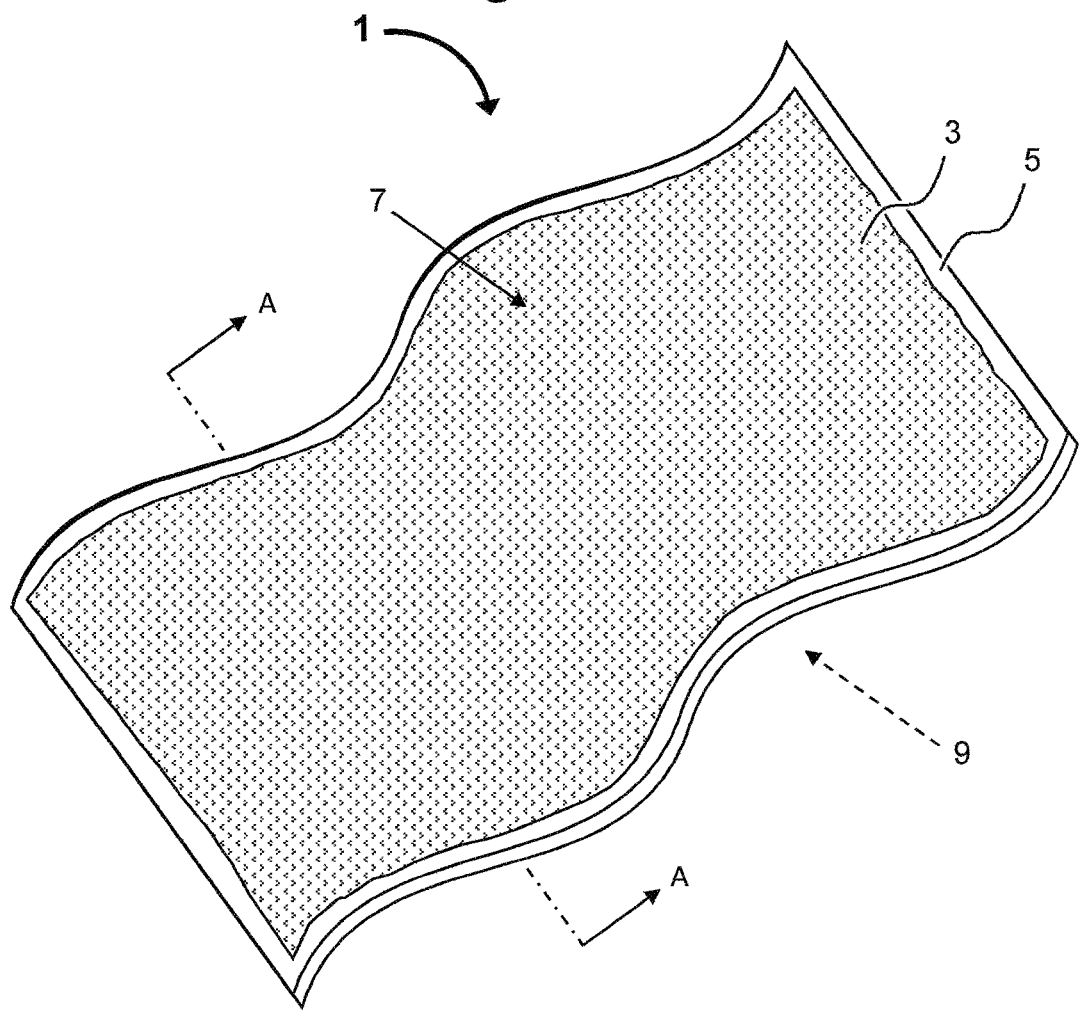
FIG. 1A is a perspective view showing an inventive flexible container combination of the present disclosure in the form of a roll-up container in an open configuration comprising an overlay at least partially disposed upon a flexible supportive base substrate.
Figure 1B:
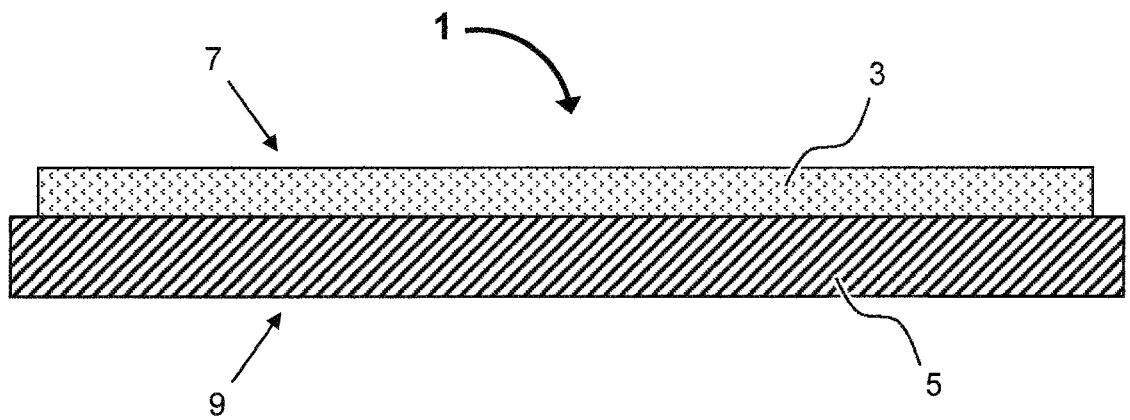
FIG. 1B is a cross-sectional view showing the inventive flexible container combination of FIG. 1A as taken along line A-A.
Figure 1C:
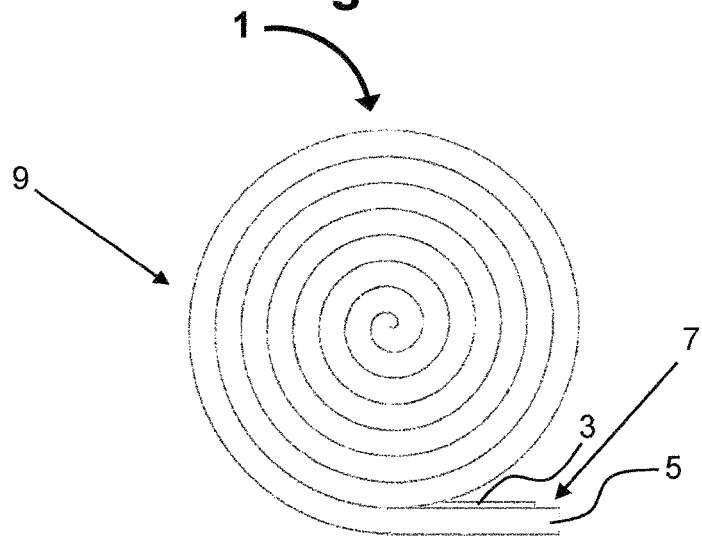
FIG. 1C is a side view showing the inventive flexible container combination of FIG. 1A in a rolled-up configuration.
Figure 2:
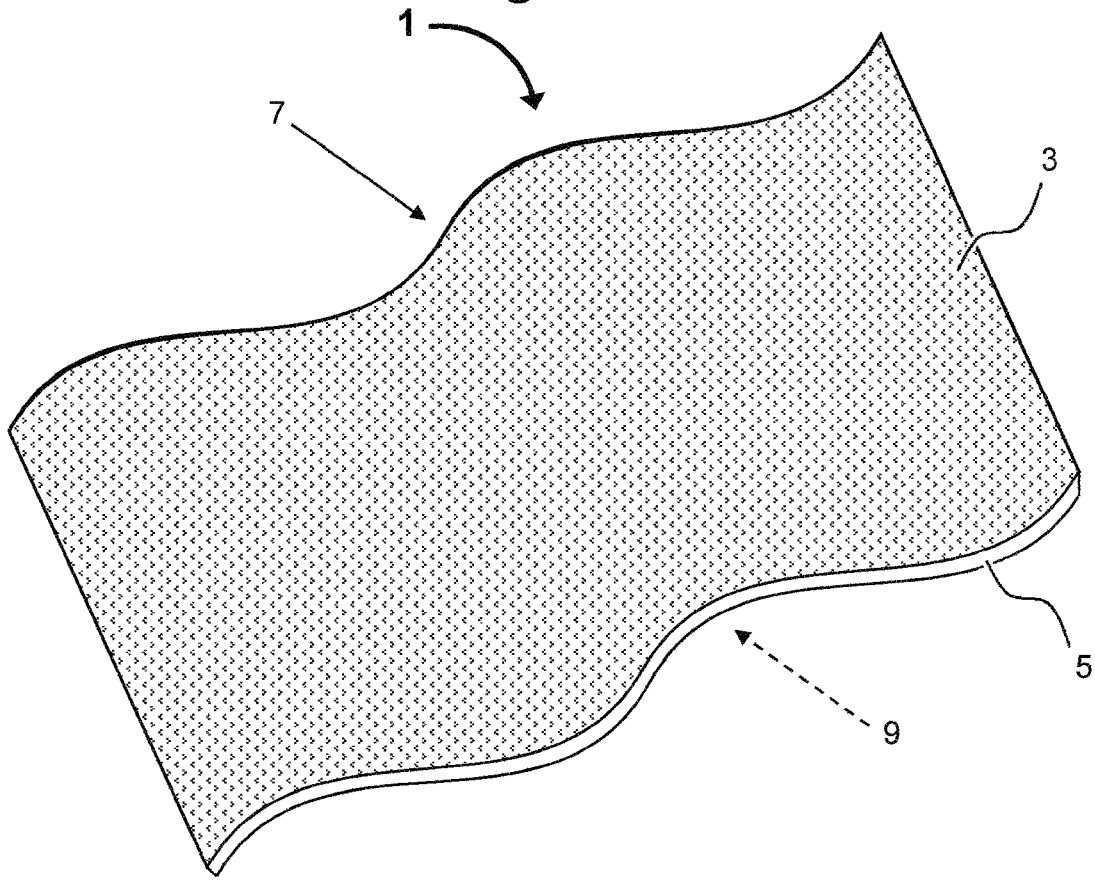
FIG. 2 is a perspective view showing an inventive flexible container combination of the present disclosure in the form of a roll-up container in an open configuration comprising an overlay disposed upon substantially an entire surface of a flexible supportive base substrate.

Repeated use of reference characters in the present specification and drawings is intended to represent the same or analogous features or elements of the present invention.

DEFINITIONS

It should be noted that, when employed in the present disclosure, the terms "a" and "an" are intended to mean "at least one" of any stated features, elements, integers, steps, components, or groups and are not intended to be limited to only one of such features, elements, integers, steps, components, or groups thereof, except where specifically stated as such. In addition, use of the phrase "at least one" is not intended to render other uses of the terms "a" or "an" to be limited to only one of a feature, element, integer, step, component, or group.

It should be noted that, when employed in the present disclosure, the terms "comprises," "comprising" and other derivatives from the root term "comprise" are intended to be open ended terms that specify the presence of any stated features, elements, integers, steps, components, or groups, and are not intended to preclude the presence or addition of one or more other features, elements, integers, steps, components, or groups thereof.

As used herein with respect to the viscoelastomeric thermoset overlay, the terms "adhesive" and "adhesiveness" refer to the overlay exhibiting tackiness to which a compatible item will stick or hold fast.

As used herein, the term "catalytic amount" is a term of the art, which is recognized by persons having ordinary skill in the art, and refers to an amount that is enough to obtain the desired response.

As used herein with respect to the viscoelastomeric thermoset overlay, the terms "cohesive" and "cohesiveness" refer to exhibiting a molecular attraction by which the molecules of the overlay are united throughout the mass such that the overlay retains its structural integrity when adhesively subjected to separating forces.

As used herein, the term "flexible" means capable of being bent into a cylinder and subsequently unbent into a laid-flat state.

As used herein, the term "reaction media" refers to the uncured mixture of chemicals which, upon curing, forms the viscoelastomeric thermoset overlay of the present invention.

As used herein, the term "reaction product" refers to the resulting product obtained upon curing the reaction media to form the viscoelastomeric thermoset overlay of the present invention.

As used herein with respect to the viscoelastomeric thermoset overlay, the terms "releasable" and "releasability" refers to the setting free from restraint or disengagement of an item from the overlay.

As used herein with respect to the flexible container combination, the term "transparent" refers to having the property of transmitting light without appreciable scattering so that items disposed within are at least partially visible from the outside such that the items can be substantially discerned.

The terms "viscoelastomeric" and "viscoelastic" are used interchangeably herein to refer to a substance having viscous and elastic properties.

These terms may be defined with additional language in the remaining portions of the specification.

DETAILED DESCRIPTION

The invention is generally directed to inventive flexible containers comprising flexible base substrates which are at least partially overlayed with an inventive adhesive, cohesive, viscoelastomeric thermoset overlay. Such inventive containers can exhibit unique viscoelastic, adhesive, cohesive, releasability, cleansability, and/or antipathogenic properties.

The unique flexible container combinations of the present invention are provided by incorporating a unique adhesive, cohesive, releasable, antimicrobial, cleansable and reusable thermoset viscoelastomeric polymer component in the form of a viscoelastomeric thermoset overlay onto a front side surface, preferably an exterior surface, of a flexible base so as to operationally interface with and engage a surface of an item disposed thereupon. In one aspect of the present invention, a particularly effective viscoelastomeric thermoset overlay component is derived from a thermoset reaction product prepared from a thermosetting reaction media comprised of a substantially uniform admixture of from about 1 percent to about 10 percent by weight (wt %) of an isocyanate prepolymer, from about 35 wt % to about 55 wt % polyols with said polyols consisting essentially of straight chain linking diols and a cross-linking triols, each having repetitive ether groups at a diol to triol weight ratio ranging from about 3:1 to about 1:3, and from about 20 wt % to about 55 wt % plasticizer containing less than about 50 wt % (with respect to the total reaction media weight) of an epoxidized triglyceride plasticizer and from about 0 wt % to about 40 wt % (with respect to the total reaction media weight) of an ester plasticizer, with the plasticizer being uniformly and cohesively dispersed and bound throughout the reaction product. Typically, the useful polyols will be comprised of liquid polyethers having a molecular weight of about 1,000 to about 20,000.

Although several exemplary embodiments of the present invention will be described herein, it should be understood that the disclosed embodiments are intended merely as non-limiting examples of the invention that may be embodied in various forms. Therefore, specific details disclosed herein, such as relating to composition, structure, function, and the like, are not to be interpreted as limiting in any manner whatsoever, but rather only as one of numerous example bases for claims and/or teaching persons having ordinary skill in the art to variously employ the present invention in virtually any appropriately detailed structure or circumstance.

The invention may be better understood with reference to the Figures. Referring to FIGS. 1A-8, the present invention provides a flexible container combination 1 comprised of a flexible supportive base substrate 5 (also referred to herein as a "flexible supportive base," or more simply as a "base") equipped with a cohesive and releasably adhesive viscoelastomeric thermoset overlay 3 (also referred to herein more simply as an "overlay") which serves to adhesively immobilize stowed items 13 adhering thereto until intentionally removed therefrom.

Continuing with FIGS. 1A-8, the flexible container combination 1 of this invention comprises a flexible supportive base 5. The flexible supportive base 5 comprises a front side 7 upon which the viscoelastomeric overlay 3 is disposed, and an opposing back side 9 distal to the front side 7. The flexible supportive base 5 provides the basic container structural support for the container combination 1, including the supportive structure for the overlay 3.

In general, the base 5 may have any desired shape (e.g., rectangular, square, trapezoidal, triangular, circular, oval, etc.) and can be appropriately sized to accommodate a particular stowed item 13 or group of stowed items. For example, in one non-limiting exemplary embodiment, the base 5 can have a generally rectangular shape having length and width dimensions of less than about 100 cm and 50 cm, respectively, such as less than 30 cm and 10 cm, respectively, or less than 10 cm and 7 cm, respectively. However, such non-limiting embodiment can have length and width dimensions which are greater than 100 cm and 50 cm, respectively, without departing from the scope of the invention. Similarly, the base 5 will have a thickness which may be uniform or non-uniform. There is no particular limit to the thickness, provided that the base 5 remains flexible and/or performs as intended by the user. For example, in one non-limiting exemplary embodiment, the base 5 can have a thickness of less than about 100 mm, such as about 1 mm to about 50 mm, or about 5 mm to about 10 mm. However, the base 5 can have a thickness that is less than about 1 mm or greater than about 100 mm without departing from the scope of the invention.

The flexible supportive base 5 may be comprised of any flexible natural or synthetic material useful in providing a suitable flexible supportive base 5 for a desired flexible container combination 1 herein. More particularly, the flexible supportive base 5 can be comprised of a host of flexible materials which provide an embedding or adhesive attraction to the viscoelastomeric overlay 3, and may be provided as a film, sheet, fabric or any other flexible material supportive of the overlay 3, as well as of any items 13 intended to be contained thereby. In addition, the base 5 can be provided in a single sheet form or as a multi-layered or composite material form. Examples of materials which can be suitable as a flexible supportive base 5 include, but are not limited to, natural, synthetic and fabricated materials such as polyesters, polyethylene, polypropylene, nylon, rayon, dacron, manila, polyethylene terephthalate, polyamides, polyurethane, linen, wool, cashmere, jute, polyacetates, polyacrylics, spandex, latex, orlon, cotton, silk, velvet, canvas, leather, fiberglass, acrylonitrile-butadiene-styrene polymers, polystyrene, metallic foils, as well as a host of other such flexible synthetic and/or natural substances which can adhesively engage or embed the overlay 3, as well as combinations thereof.

Desirably, the front side 7 (i.e., the side upon which the overlay 3 is disposed) surface of such flexible supportive base 5 materials has an overall attachment affinity to the viscoelastomeric thermoset overlay 3 which is greater than the adhesive affinity of the overlay to any items 13 intended to be stowed by the flexible container combination 1. Alternatively, the front side 7 surface of the base 5 material can have a relatively lower adhesive affinity towards the overlay 3 (as compared to any items 13 to be stowed), provided however that the front side 7 of the base 5 material comprises suitable anchoring sites (e.g., porous or woven flexible materials) such that the resultant overall attachment force between the front side 7 of the base 5 material and the overlay 3 is greater than the adhesive force between the overlay 3 and any items 13 to be stowed thereby. Persons having ordinary skill in the art will recognize that the precise attachment force between the overlay 3 and the front side 7 of the base 5 material will vary depending upon numerous factors, such as the properties of the base 5 material(s), the viscoelastomeric overlay 3 and the items 13 to be stowed, for example. Accordingly, a flexible base 5 material wherein the overall attachment force of the overlay 3 to the base 5 material is less than the overall adhesive force of the overlay 3 to an item 13 to be stowed thereby would not be a suitable material for providing the front side 7 of the base 5 of the inventive container combination 1.

Similarly, in aspects where the container combination 1 is intended to be at least partially rolled-up or otherwise folded upon itself (see e.g., FIGS. 1C, 3C, 4B, 5B, 6B and 7B), it is desirable that the front side 7 of the base 5 material has an overall attachment force to the viscoelastomeric thermoset overlay 3 which is greater than the overall adhesive force between the overlay 3 and the back side 9 of the base 5 material. Persons having ordinary skill in the art will recognize that the precise attachment force between the overlay 3 and the front side 7 of the base 5 material and the precise adhesive force between the overlay 3 and the back side 9 of the base 5 material will vary depending upon numerous factors, such as the properties of the front side 7 and back side 9 of the base 5 material(s), the type of attachment of the overlay 3 to the front side 7 of the base 5 material (e.g., adhesive bonding, in situ curing, surface properties (such as the presence of anchoring sites versus a smooth surface), etc.), and the like, for example.

Continuing with FIGS. 1A-8, the inventive flexible container combination 1 also comprises a viscoelastomeric thermoset overlay 3. In its most basic form, the viscoelastomeric thermoset overlay 3 comprises a prepolymer (e.g., a glycol prepolymer), a cross-linking polyol, a straight chain linkage polyol and a plasticizer (e.g., an epoxidized plasticizer). The viscoelastomeric thermoset overlay 3 can further comprise other additives as well, such as additional plasticizers, catalysts, colorants, UV inhibitors, and the like, without departing from the scope of the invention.

In general, the inventive viscoelastomeric thermoset overlay 3 may be appropriately sized to accommodate a particular container combination 1 and/or its stowed item(s) 13. For example, the overlay 3 may have any desired shape (e.g., rectangular, square, trapezoidal, triangular, circular, oval, random, etc.), and will typically have a similar shape to the flexible supportive base 5, though it need not be (compare e.g., FIGS. 1A and 5A). Likewise, the dimensions of the overlay 3 will typically be equal to or less than the dimensions of the flexible supportive base 5. However, an overlay 3 can also be greater than the base 5 in one or more dimensions without departing from the scope of the invention. In addition, the flexible container combination 1 can comprise a single overlay 3 or multiple overlays 3 without departing from the scope of the invention (see e.g., FIG. 8).

Similarly, the viscoelastomeric thermoset overlay 3 will have a thickness which may be uniform or non-uniform. There is no particular limit to the thickness, provided that the overlay 3 remains flexible and/or performs as intended by the user. For example, in one non-limiting exemplary embodiment, an adhesively applied overlay 3 (i.e., wherein a prefabricated overlay 3 is applied to a flexible supportive base 5) can have a thickness of less than about 10 mm, such as less than about 5 mm, or less than about 3 mm, or about 1 mm to about 9 mm in thickness, to provide the desired cohesiveness and adhesiveness for stabilizing stowed items 13 against movement. In another non-limiting exemplary embodiment wherein the overlay 3 is in a thermoset bonded form (i.e., wherein the overlay thermosetting reaction media is first applied to a flexible supportive base 5 in liquid form and then cured in situ), a lesser thickness of the viscoelastomeric thermoset overlay 3 may be effectively utilized, such as a thickness of less than about 8 mm, or less than about 4 mm, or less than about 1 mm, or about 0.3 mm to about 7 mm in thickness, to provide the desired cohesiveness and adhesiveness for stabilizing stowed items 13 against movement. It should be understood that thicker overlays 3 (i.e., thickness greater than 10 mm and 8 mm, respectively) can also be utilized without departing from the scope of the invention, such as for stowing relatively heavier items 13 for example, but are generally unnecessary.

It has been discovered that a unique thermosetting reaction media yields an inventive viscoelastomeric thermoset overlay 3 possessing unexpectedly superior properties for use in the flexible container combination 1 of this invention. Such thermosetting reaction media provides a polyurethane-based overlay 3 derived by reacting a polyisocyanate with a polyol. The thermosetting reaction media also includes a polarized organic plasticizer in prescribed amounts, as further discussed below. Particularly effective as a polarized plasticizer for use herein are epoxidized triglycerides, such as epoxidized vegetable oils, typically in amounts of less than about 50 wt % of the overall reaction media weight.

Desirably, the polyols of the thermosetting reaction media include diol and triol reactants, such as polyether diols and polyether triols having functional groups, such as hydroxyl groups, (e.g., polyoxyethylene and/or polyoxypropylene diols and triols) normally of a molecular weight in excess of 1,000 in prescribed amounts, as further discussed below.

Providing an inventive overlay 3 having desired flexibility, cohesiveness and adhesiveness efficacy when used in the flexible container combinations 1, such as depicted in FIGS. 1A-8, necessitates the preparation of a thermosetting reaction media precursor which provides a properly configured carbamate thermoset linkage (e.g., urethane). In general, the applicable thermosetting polyurethane precursor reaction media for preparing the overlay 3 includes a controlled amount of polyols (e.g., diols and triols) reacted with a ring-opening species of a hardener (e.g., amines, amides, mercaptans, anhydrides, polycyanates such as a diisocyanate, etc.). The ratio of polyol reactants, hardeners, catalyst, reaction temperatures, etc. are carefully monitored with an appropriate balance given to the diol and triol reactants to create the necessary cross and linear thermoset linkages needed in combination with selective plasticizers and amounts thereof necessary to provide the stability, cohesiveness and adhesiveness of the unique thermoset viscoelastomeric overlays 3 of this invention. Indeed, other reactants, catalysts, reaction temperatures and conditions causing an excessively cross-linked thermoset polymer coupled with insufficient straight chain bridging between the cross-linkage sites will fail to create an effective viscoelastomeric thermoset overlay 3 for use herein. The thermosetting reactants and conditions are thus selectively chosen so as to avoid excessive cross-linkage and a creation of a thermoset of an excessive glass transition temperature.

Reactants and reaction conditions which favor a more linear, cohesive and adhesive viscoelastomeric thermoset backbone structure receptive to effective polar plasticizer loading are particularly well-suited for providing the overlay 3. Since a relatively greater exothermic reaction and/or more elevated curing temperature tends to create a relatively more rigid thermoset, the reactants and reaction media conditions desirably utilize a comparatively slower reaction rate (e.g., via catalyst selection), a comparatively lower curing temperature, and a more controlled curing time, along with effective amounts of triol cross-linking to diol straight chain producing reactants in combination with effective plasticizers in prescribed amounts (as discussed further herein), all of which factors are precisely controlled in order to effectuate the desired overlay 3 properties. Such carefully controlled reaction media conditions coupled with the proper reactants and plasticizers will accordingly provide a flexible reaction product (i.e., overlay 3) having an effective quantum of cross-linkages resulting in a highly unique cohesive and releasable adhesive thermoset reaction product especially adapted for use as an overlay 3 herein.

The reactants are also suitably formulated so as to provide a thermosetting reaction media which can be effectively converted into an overlay 3 specifically adapted for use in the flexible container combination 1 of this invention. The resultant thermoset plasticized viscoelastomeric reaction product yields a labyrinth polymerizate structure which provides an overlay 3 having unexpectedly desirable cohesive and adhesive properties. The unique thermoset overlay 3 of the present invention can be further characterized as being a flexible viscoelastomeric thermoset polymer exhibiting low rebound velocity and hysteresis properties, in addition to its unexpectedly superior cohesiveness and adhesiveness. The desired overlay 3 flexibility will allow the overlay 3 to suitably mate onto the flexible supportive base 5 and operate substantially harmoniously with the flexibility attributes of the base 5. In addition, the overlay 3 can possess outstanding memory attributes.

As referenced above, the viscoelastomeric thermoset overlay 3 comprises a thermosetting reaction media prepolymer which provides a properly configured carbamate thermoset linkage (e.g., urethane). Suitable prepolymers can include ring-opening species of a hardener (e.g., amines, amides, mercaptans, anhydrides, isocyanates including polyisocyanates such as a diisocyanate, etc.). In one non-limiting exemplary embodiment, the prepolymer is a polyisocyanate prepolymer. Suitable polyisocyanates include, but are not limited to, aromatic diisocyanates (e.g., diphenylmethane diisocyanate (MDI) or toluene diisocyanate (TDI)) and aliphatic diisocyanates (e.g., hexamethylene diisocyanate (HDI) or isophorone diisocyanate (IPDI)) in a conventional prepolymer form. The prepolymer component of the thermosetting reaction media (and thus of the resulting viscoelastomeric thermoset overlay 3) will typically be present in an amount of about 1 wt % to about 10 wt % of the total reaction media weight, such as about 2 wt % to about 9 wt %, or about 3 wt % to about 8 wt %, or about 4 wt % to about 7 wt % of the total reaction media weight.

As referenced above, the viscoelastomeric thermoset overlay 3 also comprises polyols. Typically, the overlay 3 will include a straight chain linkage polyol and a cross-linking polyol in a total amount of about 35 wt % to about 55 wt % of the total reaction media weight, wherein the straight chain linkage polyol to a cross-linking polyol weight ratio is about 4:1 to about 1:4. In some desirable embodiments, the straight chain linkage polyol will be in the form of a two-functional polyol (i.e., a diol) and the cross-linking polyol will be in the form of a three-functional polyol (i.e., a triol), such as polyether diol and polyether triol reactants (e.g., polyoxyethlene and polyoxypropylene diols and triols), for example. The triols within the reaction media cause cross-linking within the resultant polymeric structure of the viscoelastomeric thermoset overlay 3 to occur by providing three available reactive functional groups (e.g., hydroxyl groups). In contrast, the diols within the reaction media provide uncrossed linkages (i.e., straight chain linkages) within the resultant polymeric structure of the viscoelastomeric thermoset overlay 3. In some aspects, certain stowable items 13 may necessitate a relatively lower adhesion level compared to other stowable items (e.g., a fragile stowable item 13). Such a relatively lower adhesion level can be accomplished by utilizing a relatively higher triol content (e.g., a diol to triol ratio of about 1:3). In contrast, a comparatively higher diol content (e.g., a diol to triol ratio of about 4:1) will provide a higher degree of adhesiveness, which may be better suited for comparatively heavier and/or more durable stowable items 13.

Exemplary effective diols and triols for the present invention include those having repetitive oxygen and hydrocarbyl groups of higher molecular chain lengths (i.e., molecular weight of at least about 1,000), such as polyethers equipped with polymerizable functional hydroxyl groupings. Suitable diol reactants include polyether diols characteristically comprised of a straight polyether molecular chain having two terminal hydroxyl groups. Suitable triol reactants include polyether triols which characteristically have two terminal and one additional cross-linking reactive hydroxyl groups which provide the polyfunctional cross-linking sites in the thermosetting reaction media.

The diols and triols, which can be especially useful in preparing the viscoelastomeric thermoset overlay 3 herein, are derived from oxygen containing hydrocarbyl diols and triols of a molecular weight of at least 1,000, and include those having repetitive oxygen containing functional groups, such as typically provided by polyester and polyether groupings. Due to the oxygen atoms' electronic need for electrons to satisfy its orbital needs, it appears that these repetitive internal oxygen-containing groupings of straight chain linkages (i.e., diols) sandwiched between cross-linkages (i.e., triols) provide ideal polarized enclaves for uniformly hosting a corresponding substantially polarized plasticizer concentration within the polymeric structure, all of which appears to collectively impart a synergistic cohesive and adhesive effect to the overlay 3.

The polyether diols and triols are commercially available at various chain lengths, typically ranging from about 1,000 to about 20,000 molecular weight. The polyether diols and triols which are most suitable herein are those which are substantially liquid at room temperature (i.e., about 21° C.) and which typically have a molecular weight of less than about 20,000, such as less than about 15,000, or less than about 10,000. Since there exists definitive manufacturing advantages in maintaining fluidity during the initial mixing and prefabricating steps when applying the thermosetting reaction media to a flexible supportive base 5, such polyols which are more fluid tend to be better suited for those applications wherein the overlay 3 penetrates into recessed or porous sections of the flexible supportive base 5. In some preferred embodiments, polyether diol and polyether triol reactants which are particularly effective for use herein include polyoxyethlene and polyoxypropylene diols and triols having a molecular weight generally ranging from about 1,000 and 10,000, more particularly such diols having a molecular weight of about 2,000 to about 6,000 and such triols having a molecular weight of about 2,000 to about 8,000, and most particularly such diols having a molecular weight of about 3,000 to about 5,000 and such triols having a molecular weight of about 2,000 to about 8,000, to provide a highly effective thermoset polymeric structure for housing the plasticizer in a highly effective cohesive and adhesive form.

As referenced above, care needs to be exercised regarding the extent of cross-linking, as well as the intervening polyoxyalkylene straight chain linkages separating the cross-linking sites. This is most effectively accomplished by retaining a diol to triol weight ratio content from about 4:1 to about 1:4, such as about 3:1 to about 1:3, or about 13:7 to about 7:13, or about 3:2 to about 2:3, so as to provide the necessary straight chain polyether linkage and cross-linkage infrastructure for the overlay 3.

The basic viscoelastomeric reaction product molecular structure requires a unique cross-linked structure by controlling the diol to triol ratio (e.g., dihydroxy polyalkylene oxide to trihydroxy polyalkylene oxide) to create a thermoset viscoelastomer having a sufficient quantum of straight chain polyether linkages. The oxygen rich diol straight chains apparently serve to effectively separate the thermoset cross-linkage and become sandwiched between the cross-linking triol polymerizate linkages, creating unique plasticizer enclaves. The reduced level of triol cross-linkages (caused by the intermittently disposed straight chain diol linkages) does not alter the overall viscoelastic characteristics of the reaction product. Apparently, the controlled thermoset structure permeating throughout the reaction mass creates sites of a controlled polar density within the cross-linked polyether polymerizates interspersed amongst straight chain polyether bridges to provide a unique labyrinth structure, which apparently provides an appropriate polarity and entrapment for an effective loading of plasticizers therein. By establishing a viscoelastomeric molecular structure loaded with properly oriented and entrained plasticizers (i.e., resulting in a non-bleeding polymer), the desired adhesive and cohesive release properties of the overlay 3 are thereby achieved. Countless enclaves of negatively charged straight chain diols and cross-linked triols appear to form a thermoset labyrinth loaded with the polarized plasticizer uniformly distributed throughout the reaction media and the cured reaction product. This unique polarized polymerizate infrastructure loaded with an effective amount of polarized plasticizer stacking within the reaction product labyrinth apparently creates a synergistic adhesive and cohesive reaction product effect.

As referenced above, the viscoelastomeric thermoset overlay 3 also comprises plasticizer. Suitable plasticizers include those commonly known in the art as plastic plasticizers, and more particularly as PVC plasticizers. In some preferred embodiments, epoxidized triglyceride plasticizers have been found to be particularly effective. Amongst the epoxidized triglyceride plasticizers suitable for use herein are the epoxidized animal oils and vegetable oils. Typically, such epoxidized triglyceride plasticizers can be present in the reaction media at levels of about 10 wt % to about 50 wt % of the total reaction media weight, such as about 20 wt % to about 40 wt % of the total reaction media weight, or about 25 wt % to about 35 wt % of the total reaction media weight. In one non-limiting exemplary embodiment, effective application of the overlay 3 to a flexible supportive base 5 was accomplished when the epoxidized triglyceride plasticizer content was about 30 wt % of the total thermosetting reaction media weight. It should be noted that since the weight of the resulting overlay 3 generally does not change from the weight of the reaction media during the curing process, the term "percent by weight of the total reaction media weight" is generally equivalent herein to the term "percent by weight of the overlay 3 weight" (and derivatives thereof).

In some preferred embodiments, epoxidized vegetable oils have been found to effectively serve as a dominant plasticizer for the inventive viscoelastomeric thermoset overlay 3, which in combination with the bridging straight chain polyether diol polymerizates, will unexpectedly create the desired flexibility, plasticization, releasability, cohesiveness and adhesiveness efficacy in the resultant cured viscoelastomeric thermoset overlay 3. Particularly effective cohesive and adhesive properties are imparted to the overlay 3 when the epoxidized vegetable oil plasticizer concentration is maintained at less than about 50 wt % of the reaction media weight, such as less than about 45 wt %, or about 10 wt % to about 50 wt % of the total reaction media weight, providing especially enhanced adhesive and cohesive stability efficacy to the overlay 3. In come desirable aspects, the epoxidized triglyceride plasticizer can be in the form of epoxidized vegetable oil, with amounts ranging from about 20 wt % to less than about 50 wt % of the total reaction media weight being highly effective for certain applications. Although the applicable epoxidized vegetable oil plasticizer may include a variety of epoxidized vegetable oils (e.g., castor, corn, cotton seed, palm, safflower, linseed, soybean, coconut, olive, peanut, rapeseed, canola, etc.), it has been discovered herein that in some preferred embodiments, epoxidized soybean oils are particularly effective as the epoxidized vegetable oil plasticizer component when preparing the reaction product to form the thermoset viscoelastomeric overlay 3.

Although the viscoelastomeric thermoset structure is especially adapted to loading with a host of plasticizers, it has been found that polar plasticizers (e.g., epoxidized triglycerides), which create a polar attraction between the oxygenated viscoelastomeric polymeric chain linkage and the plasticizer, are particularly desirable. This molecular electronic attraction apparently contributes to the unique adhesive and cohesive properties of the reaction product and the resultant overlay 3 therefrom. Since the plasticizers are not effectively loadable onto a cured thermoset viscoelastomer, the plasticizing reagents are necessarily uniformly incorporated into the thermosetting viscoelastomeric reaction media prior to curing, to provide a uniform and homogeneous polarized distribution thereof throughout its entire uncured composition. The thermosetting conditions of the reaction media apparently uniformly align and create a synergistic polar positioning and alignment between the polar attracting polymeric chain sections of the thermoset reactants and the plasticizer to provide a highly effective adhesive polarized plasticizer loading and alignment thereof within the resultant overlay 3. This permits a tenacious and cohesive plasticizer loading without any evidence of plasticizer seepage or separation (i.e., plasticizer bleeding) from its hosting thermoset viscoelastomeric polymeric structure, as well as from the overlay 3 derived therefrom.

As referenced above, it has been discovered herein that epoxidized vegetable oils are particularly effective in providing the desired adhesiveness, cohesiveness and plasticization to the resulting viscoelastomeric thermoset overlay 3. Such epoxidized vegetable oils can be particularly effective in contributing towards the desired flexible viscoelastic properties herein. In some aspects, an epoxidized vegetable oil may constitute the majority constituent by weight of the viscoelastomeric thermoset overlay 3 (i.e., the greatest amount by weight of the total reaction media weight), but is desirably maintained at a level of less than about 50 wt % of the total uncured reaction media weight, such as about 25 wt % to about 45 wt % of the total reaction media weight, or about 30 wt % to about 40 wt % of the total reaction media weight.

In preparing an overlay 3 formulated with a vegetable oil, the reaction media typically includes a measured amount of a triglyceride component (e.g., epoxidized fatty triglycerides) with the triglyceride amounting to less than about 50 wt % of the total reaction media weight, along with an effective amount of the straight chain thermosetting component, such as provided by the polyether diols. Surprisingly, by reducing the triglyceride oil (e.g., epoxidized triglyceride oil) content and increasing a proportionate amount of the straight chain forming thermoset reactants, it has been found herein that the cured cohesiveness, tackiness (i.e., adhesiveness) and overall efficacy of the resultant overlay 3 can increase, even though the reaction media may still contain the triglyceride component (e.g., epoxidized soybean oil (ESO)) as the majority reaction media component by weight.

Compared to conventional shock absorbing formulations (which tend to bleed plasticizer), it has been discovered herein that increasing the compositional cohesiveness and adhesiveness of the overlay 3 while alleviating plasticizer bleeding can be accomplished with an epoxidized oil content of less than about 50 wt % of the total reaction media weight, coupled with a substantial decrease in the cross-linking triol reactant, which leads to a reduction in cross-linkage and a concomitant increase in straight chain structure as provided by the straight chain producing diol reactant. The polymeric molecular change within the thermoset reaction product (with or without the use of other conventional plastic plasticizers in addition to the epoxidized triglyceride) apparently creates a localized intramolecular polarity charge which is effectively expressed by the unique oxygen containing viscoelastomeric polyether backbone structure intertwined within the cured reaction product mass, all of which leads to a highly effective polarized plasticizer loading, to yield an unexpectedly desirable viscoelastomeric adhesive and cohesive overlay 3 possessing highly effective release and non-bleeding properties. Accordingly, effective cohesive and adhesive efficacy for the overlay 3 can be achieved at a triglyceride plasticizer content ranging from about 15 wt % to less than about 50 wt % of the total reaction media weight.

In some aspects, the addition of, or substitution of at least some of the triglyceride plasticizer (e.g., epoxidized triglycerides) with, a viscosity reducing ester plasticizer can effectively maintain cohesiveness and adhesiveness of the overlay 3 while also providing excellent flexibility, releasability and stability properties. Certain polar ester plasticizers having a fluid consistency at room temperature (i.e., about 21° C.), and typically those of a relatively low molecular weight (i.e., a molecular weight of about 750 or less) can effectively contribute to exceptional working viscosities during the initial curing stages, rendering prefabrication of the reaction media into the desired overlay 3 much easier.

In some aspects, such lower molecular weight (i.e., molecular weight of less than about 750) plasticizers (e.g., ester plasticizers) can be effectively utilized to create a less viscous thermosetting reaction media (as compared to using epoxidized triglyceride plasticizer alone). For example, the addition of, and/or partial substitution of the epoxidized triglyceride plasticizer with, a lower molecular weight ester plasticizer can significantly increase fluidity and workability of the thermosetting reactants, while also retaining other desirable thermoset attributes of the overlay 3. Such ester plasticizers (particularly such lower weight ester plasticizers) coupled with a controlled diol to triol ratio, and in combination with the epoxidized triglyceride plasticizer, can be effectively utilized to provide a reaction media which will tenaciously cure and bond in situ to a host of flexible supportive bases 5. For most such in situ curing applications, the weight ratio of epoxidized triglyceride plasticizer to ester plasticizer (if present) can generally range from about 8:1 to about 1:3, such as from about 4:1 to about 1:1. The molecular size, configuration, polarity, functional molecular groups, etc. of the thermosetting polymeric reactants, along with a combination of such lower molecular weight ester plasticizer, and the epoxidized vegetable oil in measured amounts (as prescribed herein) collectively contribute towards the creation of a viscoelastomeric thermoset overlay 3 possessing desired unique cohesive and adhesive properties.

As referenced above, the overlay 3 is comprised of an effective amount of long chain polyether polymeric linkages coupled with the appropriate prepolymer (e.g., diisocyanate) and triol cross-linkages to provide a polymeric chain of a desired polarity having an unexpectedly high affinity for a loading of polar plasticizing components within the thermoset viscoelastomeric reaction product infrastructure. In some desirable embodiments, the total plasticizer concentration (i.e., epoxidized and non-epoxidized plasticizers) can typically range from about 10 wt % to about 55 wt % of the total reaction media weight, such as about 20 wt % to about 45 wt % of the total reaction media weight, or about 25 wt % to about 40 wt % of the total reaction media weight. When additional non-epoxidized plasticizers (i.e., in addition to the epoxidized triglyceride plasticizers) are present, the weight ratio of epoxidized plasticizer to non-epoxidized plasticizer can desirably range from about 1:0 to about 1:1, such as from about 6:1 to about 3:1.

The selection of a particular non-epoxidized plasticizing agent, and its concentration, can have a pronounced viscosity effect during application of the thermosetting reaction media to a flexible supportive base 5. For example, adding a suitable ester plasticizer (e.g., by reacting an alcohol with a fatty acid) to the reaction media can serve to lower the viscosity of the reaction media. In addition, certain of the ester plasticizers (e.g., dibutyl sebacate) may be effectively used to prepare a thermosetting reaction media which provides exceptional thermosetting viscosity characteristics, which in turn can, for example, render an uncured reaction media especially suitable for direct application to the flexible supportive base 5 and then curing in situ. Other suitable ester plasticizers can be derived from the ester condensation product of an alcohol (e.g., $C_1$-$C_{18}$) with a polycarboxylic acid. Such ester plasticizers can be advantageously utilized in preparing a thermosetting reaction media which provides a thermoset viscoelastomeric reaction product having an adhesiveness tailor-made for a particular end use. For example, certain applications may require a tenacious adhesiveness (e.g., for securing a pipe wrench within the flexible container combination 1), whereas other applications may require a comparatively milder adhesiveness (e.g., for securing a fragile item within the flexible container combination 1).

In general, those plasticizers which are suitable as plasticizing agents for the plasticization of polyvinyl chlorides can be utilized as additional non-epoxidized plasticizers for the reaction media herein. In some aspects, the polar strength (often referred to as "dipole moment") of such ester plasticizers depends, to a certain degree, upon the alcohol condensation reactant chain length, which can also have an effect upon the adhesive characteristics of the thermoset viscoelastomeric reaction product. For example, non-epoxidized plasticizers having a relatively high dipole moment (e.g., dibutyl sebacate, having a dipole moment of 2.48 debyes (D), as compared to epoxidized plasticizers having a dipole moment near 0 D) can be effective in retaining the desired properties of the polymerizate while also providing a thermosetting reaction media exhibiting a reduced working viscosity, which is particularly effective for use in permeating porous interstices or fabric structures of a flexible supportive base 5. Illustrative of such additional non-epoxidized plasticizing agents include, but are not limited to, ester plasticizers, such as sebacates, adipates, terephthalates, dibenzoates, glutarates, phthalates, azelates, and the like. Such ester plasticizers may be effectively co-blended with the epoxidized triglyceride plasticizer(s) into the thermosetting reaction media, such as to create or modify the working viscosity of the reaction media. Ester plasticizers having a dipole moment of greater than 1.5 D, such as greater than 2.0 D, may be effectively utilized for this purpose. Illustrative ester plasticizing agents having a suitable dipole moment include dibutyl, dimethyl, and diethyl esters of sebacates, adipates, isophthalates, phthalates, maleates, azelates, and glutarates. It has been discovered herein that the incorporation of a lower molecular weight ester plasticizer (i.e., a molecular weight of less than about 750), such as a polyalkylene ester plasticizer), in combination with the epoxidized triglyceride plasticizer, can accordingly be utilized to provide for effective penetration of the reaction media into a flexible supportive base 5 without adversely affecting the other unique properties of the overlay 3.

One advantage of the inventive viscoelastomeric thermoset overlay 3 herein includes, inter alia, its ability to prevent seepage or bleed-out of the plasticizer, despite its relatively high plasticizer content (i.e., greater than about 10 wt %), which resolves a long-standing problem encountered by other polymers having similar plasticizer contents. In order to achieve a highly effective, stable, cohesive and adhesive overlay 3, a proper proportional amount of cross-linkages and straight chain linkages is necessary. The thermoset polymeric structure of the overlay 3 necessitates a controlled quantum of cross-linked structure, along with a controlled quantum of intervening straight chain polar attracting linkages, to impart a highly flexible viscoelastomeric backbone chain of an appropriate polarity for the hosting of polarized plasticizers. This creates an intertwining backbone chain providing excellent attractive polar sites for the cohesive polar alignment of the plasticizing agent throughout the entire viscoelastomeric mass. Such an intertwining backbone chain comprising both triols and diols helps prevent the plasticizers from bleeding-out of the viscoelastomeric thermoset overlay 3.

Achieving adhesive and cohesive efficacy requires control between molecular cross-linkage and polar alignment of straight chain thermoset moieties of a bridging structure, as well as the content and type of plasticizer, within the thermosetting reaction media to create an overlay 3 exhibiting the unexpected attributes of the invention. It has been discovered herein that an excessively high triol reactant level and/or an insufficient plasticizer content can result in an overlay 3 that is undesirably firm and less tacky (i.e., insufficient viscoelasticity and adhesiveness), while an excessively high diol reactant level can result in an overlay 3, upon contacting a stowed item 13, which becomes excessively bonded to the stowed item 13 (i.e., insufficient releasability). Through a judicious control of the plasticizer content and the diol to triol ratios as prescribed herein, a viscoelastomeric thermoset reaction product uniquely suited for use as an overlay 3 of the present invention can be achieved. In addition, it has been discovered herein that an appropriate plasticizer content, in combination with a sufficient amount of polyether diol, within the thermosetting reaction media serves to increase cohesiveness, tensile strength, softness and flexibility of the resultant overlay 3. A prescribed polyether diol to polyether triol ratio, in combination with prescribed amounts of the plasticizer, provides a unique adhesive and cohesive stability which effectively allows the overlay 3 to functionally possess a desirable cohesive releasability towards stowed items 13, even when such items 13 are stowed over prolonged time intervals (e.g., at least one year). It has also been discovered herein that the loading of the reaction media with a lower molecular weight polar plasticizer (i.e., less than a molecular weight of about 750) can permit for a reduction in epoxidized plasticizer content, which in combination with an appropriate amount of thermoset polyether straight chain linkages, can provide an overlay 3 possessing a desired stowing adhesiveness and cohesive releasability efficacy for use in the inventive flexible container combination 1 herein. In addition, the use of such lower molecular weight plasticizers can also provide a more fluid and workable curing reaction media, which may be more easily combined or bonded with the flexible supportive base 5 to provide the desired flexible container combination 1.

As referenced above, the diols and polyols (e.g., triols) of an appropriate molecular weight (as discussed above) can effectively serve as straight chain building and cross-linking components, respectively, within the cured thermoset viscoelastomeric polymeric structure. When properly controlled, they provide a plasticizer friendly, non-bleeding viscoelastomeric polymeric structure of straight chain and cross-linked linkages of an appropriate polymerizate configuration and molecular polarity for effective plasticizer loading. In contrast to conventional polymers having similar plasticizer contents (e.g., impact absorbing viscoelastomeric thermoset reaction products) which fail to retain plasticizer loading (and thus tend to leak plasticizer), the viscoelastomeric thermoset overlays 3 herein exhibit a high cohesiveness which is resistant to plasticizer leakage. The prescribed diol to triol ratio herein enables a controlled proportion of polarized plasticizing component loading to effectuate the superior adhesiveness and cohesiveness within the carefully structured thermoset reaction product, creating a polarized polymeric infrastructure which tenaciously traps and prevents plasticizer bleeding (i.e., leakage). To achieve the necessary plasticizing adhesive and cohesive efficacy, the straight chain diol precursors desirably have a relatively high polyether molecular weight (e.g., a molecular weight of about 2,000-10,000), which at an increased reaction media concentration, creates an effective linear thermoset polymeric polyoxy structure having an appropriate chain length, while also serving to substantially lessen the polymeric cross-linkage density. In general, the desired plasticizer retention and viscoelastomeric flexibility, along with the desired adhesiveness and cohesiveness, may accordingly be effectuated via interpolymerizing effective amounts of the thermosetting diols and triols of an appropriate chain length (i.e., a molecular weight of about 2,000-10,000), along with a thermosetting isocyanate (e.g., diisocyanate) reactant and plasticizer cofactors at the appropriate reaction media amounts (as prescribed herein).

In general, the thermosetting viscoelastomeric reaction media is formulated with an appropriate level of cross-linking and straight chain reactants containing a sufficient amount of polarized plasticizer to create the unique highly cohesive and adhesive viscoelastomeric overlay 3. As pointed out in U.S. patent application Ser. Nos. 15/731,815, 14/999,722 and 62/231,004 (which have been incorporated herein by reference), a viscoelastomeric reaction media favoring a substantially lower cross-linkage, loaded with an effective amount of epoxidized vegetable oil plasticizer, has been found to unexpectedly dramatically increase the adhesiveness and cohesiveness of the overlay 3. It has also been discovered that additional commonly used polarizing plasticizing agents which are chemically unreactive with the viscoelastomeric reaction media reactants can also be effectively used to impart a high degree of adhesiveness and cohesiveness to the reaction product. Such additional plasticizing agents, in conjunction with the epoxidized vegetable oil plasticizer, can also be effectively used to impart enhanced tensile strength and softness to the viscoelastomeric thermoset overlay 3, while also providing a thermosetting reaction media having a desirable viscosity and workability that is useful in the manufacture of the flexible container combination 1 equipped with the inventive overlay 3.

Procedurally, the reaction product which forms the viscoelastomeric thermoset overlay 3 can be prepared from a thermosetting reaction media homogeneously loaded with plasticizer(s) which desirably includes an epoxidized vegetable oil (i.e., from about 10 wt % to about 50 wt % of the total reaction media weight), as well as any other effective polar plasticizer, coupled with a carefully measured molar ratio of cross-linking polyols to straight chain producing polyether diols to create the necessary bridging therebetween, and an isocyanate prepolymer hardener (e.g., diisocyanate, such as aliphatic, aromatic, heterocyclic, etc., polyisocyanates, and cycloaliphatic and arylaliphatic diisocyanates) in the presence of an appropriate catalyst (e.g., preferably a relatively slow acting catalyst). The reaction media desirably contains the necessary plasticizer loading specifically adapted to provide a curable reaction media, which upon curing, produces a viscoelastomeric reaction product having a unique polymerizate structure effectively loaded with polar oriented plasticizers uniformly and homogeneously distributed throughout its entire thermoset mass, intertwined therewithin, and supported by the flexible plasticizer entrapping thermoset polymerizate structure. Suitable catalysts include tertiary amines, tertiary phosphines, strong bases (e.g., alkali, alkaline earth metal hydroxides, alkoxides, phenoxides, acidic metal salts of strong acids, metal chelates, metal alcoholates, metal phenolates, organic acid salts, organo metallic derivatives, etc.). In one particular example, an organobismuth catalyst was utilized, available under the trade name COSCAT 83 (available from Vertellus Holdings LLC, having a place of business located in Zeeland, Mich., USA). Under the most effective thermosetting and fabricating conditions, the thermosetting polymerizate precursors and the plasticizers are collectively provided in the reaction media as liquids at room temperature (i.e., about 21° C.) without necessitating the use of any solvents, other chemical dispersion aids or elevated temperatures, in order to homogeneously disperse the reaction media components. Accordingly, this allows the thermosetting reaction to be effectively conducted at room temperature.

Imparting desired flexibility, adhesive and cohesive characteristics to a viscoelastomeric thermoset overlay 3, coupled with the compatibility of a secure bonding to the flexible supportive base 5, may be effectively obtained by preparing a reaction media containing about 15 wt % to about 30 wt % of the total reaction media weight of a two functional polyether polyol (e.g., ELASTOCAST C-4057 polyether diol, available from BASF Corporation), about 15 wt % to about 35 wt % of the total reaction media weight of a three functional polyether polyol (e.g., ELASTOCAST C-4018 polyether triol, available from BASF Corporation), about 4 wt % to about 10 wt % of the total reaction media weight of methylene diphenyl diisocyanate-based glycol prepolymer (e.g., ELASTOCAST TQZ-P23 available from BASF Corporation, or ISONATE 2181 available from Dow Chemical Company, or RUBINATE 1790 available from Huntsman International LLC), an epoxidized soybean oil in an amount ranging from about 25 wt % to less than about 50 wt % of the total reaction media weight, along with a catalytic amount of a suitable catalyst (e.g., a Bismuth (3+) neodecanoate, such as COSCAT 83 available from Vertellus Holdings LLC) typically at a catalytic concentration ranging from about 0.1 wt % to about 0.6 wt % of the total reaction media weight.

In some desirable embodiments, the viscoelastomeric thermoset overlay 3 can be prefabricated prior to placement upon the flexible supportive base 5. This can be accomplished, inter alia, by disposing liquid reaction media (i.e., uncured or partially cured) into a mold and then curing the reaction media to form the overlay 3, or by pouring and curing a layer of the reaction media and then cutting strips from the layer to form the overlay 3. Other methods for forming the overlay 3 which will be apparent to persons having ordinary skill in the art are also suitable, without departing from the scope of the invention.

It has been discovered herein that certain polymeric materials, such as halogenated polymers (e.g., polyvinylchloride (PVC)) (except for special formulations) are generally adhesively incompatible with the adhesive properties of the inventive viscoelastomeric thermoset overlays 3 (i.e., the overlay 3 does not adhere well to such materials). As a result, such incompatible materials can provide excellent release properties from the overlay 3, which renders such incompatible materials particularly effective for use as a mold material which can be utilized to cure the overlay reactants and thus prefabricate the overlays 3. However, it should be understood that if such incompatible materials have a porous or fabric structure, such porous or fabric structures can provide anchoring or penetration sites for the overlay 3, thus rendering such materials to be unsuitable for use as a mold material (and therefore more suitable for use as a flexible supportive base 5 herein).

Where it is desirable to utilize thermosetting reactants which provide a workable viscosity range for the prefabrication of a cured reaction media into a useful overlay 3 form, those diols and triols, as well as plasticizers, which are generally fluid at room temperature (i.e., about 21° C.) can provide a workable thermosetting viscosity range to achieve this objective. The resultant thermoset overlay 3 having controlled cross-linkages and straight chain linkages, in combination with a controlled plasticizer content homogeneously distributed throughout the thermoset polymeric network, unexpectedly imparts desirable flexibility, adhesiveness and cohesiveness, all of which renders the viscoelastomeric thermoset reaction product of the reaction media exceptionally effective as an overlay 3 herein.

In some desirable embodiments, the viscoelastomeric thermoset overlay 3 can be in the form of a prefabricated component. As reference above, the adhesive and cohesive attributes of a prefabricated overlay 3 can permit for its adhesive attachment to a flexible supportive base 5. Accordingly, films, sheets, pads, etc. of the overlay 3 may be directly adhesively secured to a supportive base 5 to provide the flexible container combination 1 herein. This may be useful for certain applications, such as wherein it is desired to convert a conventional (i.e., non-adhesive) flexible container into the flexible container combination 1 of this invention. Such conversion may be accomplished by adhesively applying a strip, film, pad, etc. of the overlay 3 to the flexible substrate of conventional flexible containers. Such a procedure could even advantageously be utilized by consumers, wherein the consumer could first obtain the viscoelastomeric thermoset overlay 3 from a manufacturer, and then apply the overlay to a flexible supportive base 5, or to a conventional flexible container, to form a flexible container combination 1 of the present invention.

In other desirable embodiments, the viscoelastomeric thermoset overlay 3 can be formed directly upon the flexible supportive base 5. This can be accomplished, inter alia, by disposing liquid reaction media (i.e., uncured or partially cured) upon the front side 7 surface of the flexible supportive base 5, and then curing the liquid reaction media in situ to form an overlay 3 that is firmly bonded (e.g., chemically and/or adhesively) to the base 5. Although this may be procedurally impractical for household consumers to perform, it provides a highly effective means for manufacturing the flexible container combination 1 herein. Many synthetic and natural textiles, such as suede leather, foam, or the woven or knitted fabrics (e.g., aertex, aida, baize, batiste, birds eye, knit, bombazine, brocade, buckram, cable knit, calico, cambric, charmeuse, chenille, corduroy, casement, cheese cloth, cheviot, chiffon, chino, chintz, crepe, crewel, damask, denim, dimity, drill, double knit, duck or canvas, felt, fiberglass, filter, flannel, flat, or, jersey knit, fleece knit, foulard, fustian, gabardine, gauze, georgette, gingham, grey or greige, industrial, intarsia knit, interlock, stitch knit, jacquard knit, Kashmir, silk, khadi, khaki, lame, laminated, lawn, leno, linsey-woolsey, madras, madras, muslin, net, mousseline, muslin, narrow, organdy, organza, oxford, percale, plain, pointelle knit, poplin, purl knit, quilted, raschel knit, reflective, rib, stitch knit, satin or sateen, shantung, sheeting, sliver knit, taffeta, stretch, tartan, terry knitted, terry, cloth ticking, tissue, tricot knit, velour knitted, velvet, voile, warp knitted, whipcord, etc.) can provide exceptional flexible supportive base 5 anchoring sites for tenaciously anchoring the overlay 3 in situ thereto. For example, this may be accomplished by first applying an uncured or partially cured overlay thermosetting reaction media to front side 7 of a fibrous flexible supportive base 5, and then curing it while present on the flexible supportive base 5 to form the flexible container combination 1. In some aspects, the uncured reaction media precursor for the overlay 3 may be suitably formulated so as to limit its penetration onto a porous or woven fabric structure of the flexible supportive base 5, such as to prevent soak-through. Accordingly, upon curing, the overlay 3 becomes firmly anchored to the front side 7 surface of the supportive flexible fabric base 5, leaving the opposing back side 9 surface uncoated. Such anchoring of the overlay 3 to the flexible supportive base 5 will tend to exhibit a higher attachment force to the flexible supportive base 5 as compared to merely adhering a prefabricated overlay 3 to the base 5 by virtue of the overlay's inherent adhesive properties. By combining the anchoring features of fabrics having anchoring sites (e.g., porous or fibrous fabrics), particularly those which possess an otherwise relatively low adhesive attraction towards the adhesive overlay 3, a flexible roll-up container combination 1 can be achieved which can be more easily rolled-up and unrolled without separation of the overlay 3 from the flexible supportive base 5. For example, the viscoelastomeric thermoset overlay 3 can be embedded into a shock absorbing porous flexible supportive base 5 (e.g., a porous rubber, a foam, etc.) to form an inventive flexible container combination 1 that is useful for protecting fragile adhered items 13. Thus, the viscoelastomeric overlay 3 of the present invention can be effectively combined as a coating and/or as an embedded overlay 3 without departing from the scope of the invention.

Regardless of whether the viscoelastomeric thermoset overlay 3 is applied to the front side 7 of the flexible supportive base 5 as a prefabricated component, or is cured in situ onto the front side 7 of the base 5, it is desirable that the overall attachment force between the overlay 3 and the front side 7 of the base 5 is greater than the adhesive force between the overlay 3 and any items 13 attached thereto (including the back side 9 material of the base 5, in the case where the flexible container combination 1 is rolled-up upon itself).

Within certain cohesive and adhesive limits, the desired level of adhesion for any overlay 3 may depend to a certain extent upon the type of flexible container combination 1 and item(s) 13 to be stowed therein. The size, delicacy, configuration and weight of the stowed item(s) 13 will generally establish which releasable adhesive strengths are best suited for any particular flexible container combination 1 end use, or for the intended item 13 to be stowed. For example, fragile items (e.g., Christmas tree decorations, glass articles, medications, etc.) will typically require a comparatively lower degree of adhesiveness of the overlay 3 than would be required by other more durable stowed items. Similarly, a heavy item 13 (e.g., a hammer) 13 may require a comparatively higher degree of adhesiveness of the overlay 3 than would be required by other less substantial stowed items. However, excessive overlay 3 adhesiveness to a stowed item 13 may cause the flexible combination 1 to fail, such as wherein removal of the stowed item 13 causes the overlay 3 to separate from the flexible supportive base 5. Thus, it is desirable that the overall attachment attraction between the viscoelastomeric thermoset overlay 3 and the flexible supportive base 5 should exceed the adhesive attraction of the overlay 3 to any given stowed item 13.

Another unique advantage of the inventive flexible container combination 1 herein resides in the manner in which the viscoelastomeric thermoset overlay 3 feature will adhesively interact with items 13 which are adhesively attached thereto. The overlay's 3 adhesive interaction with stowed items 13, when such items are placed thereupon, typically exhibits a slight initial increase in adhesiveness within about 5 to about 10 seconds after the initial adhesive attachment of an item 13 to the overlay 3, which is then followed by a stabilization to about 90% of its maximum or ultimate adhesive attraction within about 60 seconds after the initial adhesive attachment of an item 13 to the overlay 3. This slight change in adhesiveness may be indicative of an intermolecular realignment, coordinate covalent bonding, polarization of the plasticizing components, or some other molecular interaction therewithin. This subsequent adhesive increase may also be due to the viscoelastomeric properties of the overlay 3, which due to adhesive cradling of an adhered item 13, will provide added interfacing surface contacting area with the adhered item 13, resulting in an increase and subsequent stabilization of the adhesive attraction therebetween.

Since the inventive thermoset viscoelastomeric overlay 3 characteristically possesses an extremely high internal cohesiveness (i.e., the overlay 3 does not tear or otherwise internally separate from itself when an item is detached from the overlay 3), the overlay 3 is uniquely useful for diverse needs requiring a releasable, high tensile strength adhesive which fully retains its innate structural integrity upon adhesive release. As evidenced from the aforementioned, the most suitable adhesive strength for the overlay 3 for any given flexible container combination 1 ultimately depends upon its intended end usage.

As referenced above, flexible container combinations 1 equipped with a flexible supportive base 5 desirably have a comparatively lower adhesive attraction towards the back side 9 material/surface of the base 5 than for the front side 7 surface of the base 5. This feature allows the flexible container combination 1 to be rolled-up upon itself, such as for more secure containment of items 13, ease of storage, and the like (see e.g., FIGS. 1C, 3C, 4B, 5B, 6B and 7B). However, if the overlay 3 is insecurely secured to the front side 7 of the flexible supportive base 5, there exists a tendency for the overlay 3 to separate from the supportive base 5, especially upon unrolling or upon removal of an adhered item 13 therefrom. Since it is most desirable to cleanly separate an adhesively restrained item 13 from the overlay 3 without causing the overlay 3 to separate from the flexible supportive base 5, certain precautions can be undertaken to ensure that a more secure bonding of the overlay 3 to the supportive base 5 occurs. Although mechanically securing (e.g., via sewing, framing, etc.) the overlay 3 to the flexible supportive base 5, or the use of a protective cover 8 of a low adhesiveness to facilitate unrolling separation between the overlay 3 and the supportive base 5, may be used, certain fabric-based flexible supportive bases 5 can provide excellent anchoring or embedding sites for more securely bonding the overlay 3 thereto. Accordingly, in some aspects, fabrics having a reduced adhesive attraction towards the overlay 3, but which has a front side 7 comprising anchoring sites, may nonetheless be used to provide a suitable flexible supportive base 5 for the flexible roll-up container combination 1 that may be more easily rolled and unrolled. It should be noted, however, that stowed items 13 within the rolled up flexible container combination 1 will also serve as a separating barrier between the back side 9 of the supportive base 5 and the adhesive overlay 3, thus assisting the rolling and unrolling thereof.

Figure 8:
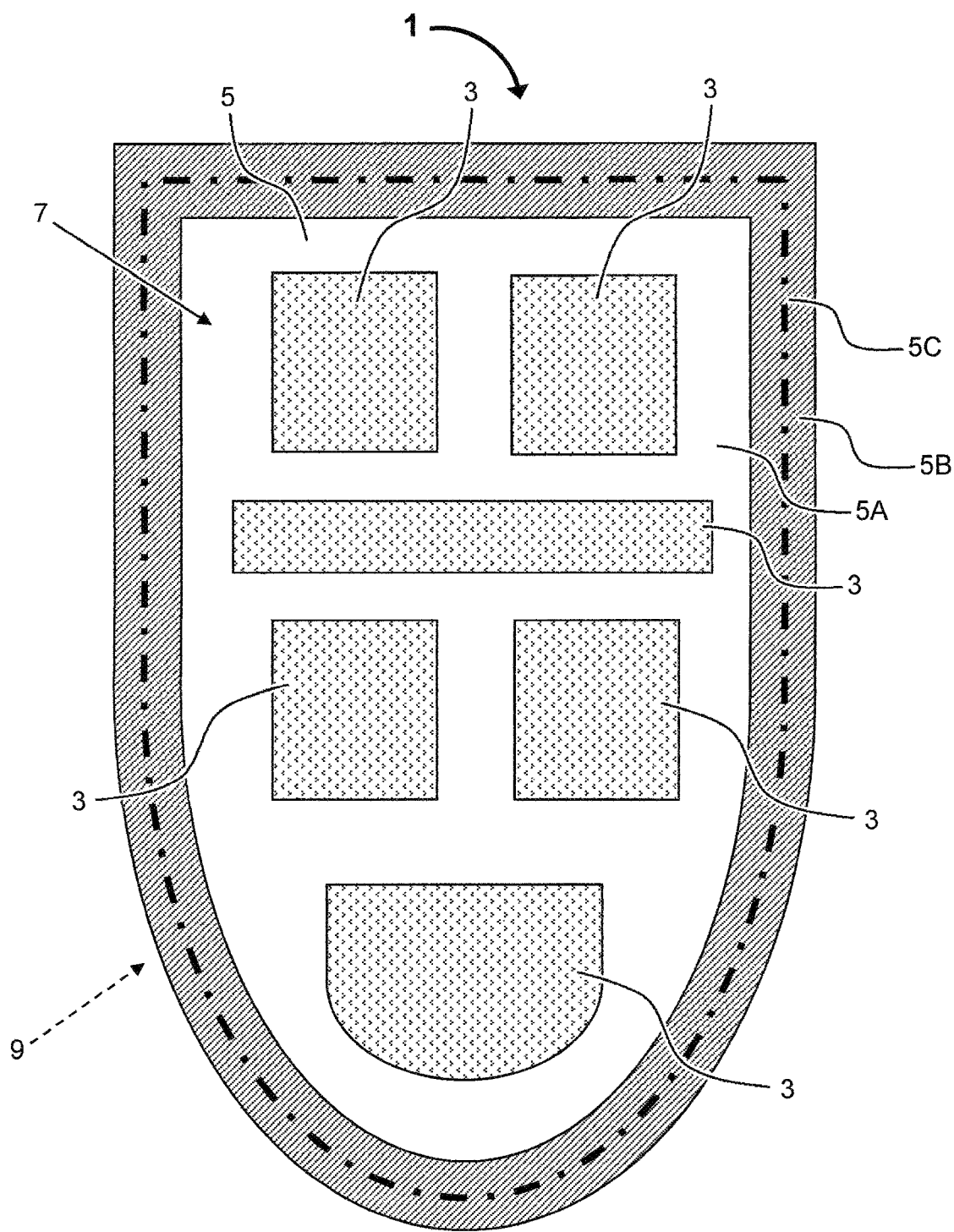
FIG. 8 is a top view showing an inventive flexible container combination of the present disclosure in an open configuration comprising multiple overlays disposed upon a front side base layer of a multilayered flexible supportive base, wherein the back side base layer is folded over onto the front side base layer and stitched into place.

In some aspects, it may be desirable to utilize a cohesive and adhesive overlay 3 in flexible roll-up container combinations 1 wherein the overlay 3 is utilized not only to immobilize stowed items 13 against movement, but also as an adhesive binder which adhesively binds the flexible container combination 1 in a rolled-up form, while also permitting a cohesive release and unwinding of the flexible roll-up container combination 1 (i.e., allowing it to unroll). Achieving a more effective rolling and unrolling efficacy for the roll-up containers 1 may be accomplished in a number of different ways, as will be apparent to persons having ordinary skill in the art. One such method entails reducing the adhesive attraction between the back side 9 of the supportive base 5 and the overlay 3 (as compared to the front side 7). This can be accomplished, for instance, by utilizing a supportive base 5 wherein the front side 7 comprises a material which has a higher overall attachment force to the overlay 3 than the material of the back side 9. For example, the front side 7 of the base 5 can comprise a porous or otherwise anchoring surface for embedding or anchoring the overlay 3 thereto, while the opposing back side 9 can comprise a surface that is smooth and has a comparatively less or reduced adhesive attraction towards the overlay 3. For demonstration purposes only, in one more particular example, the front side 7 of the flexible supportive base 5 can comprise a woven cotton or cotton polyester blend serving to anchor or embed the overlay 3, while the opposing back side 9 of the flexible supportive base 5 can comprise a laminated film having a reduced adhesive affinity towards the overlay 3. Exemplary thereof is a supportive base 5 comprised of a laminated composite of a polyvinyl-chloride film (serving as the back side 9 of the base 5) laminated to a woven cotton and polyester blend (serving as the front side 7 of the base 5), thus providing a laminated composite composed of two different flexible materials exhibiting two different affinities towards the overlay 3, all of which may be effectively utilized to provide a roll-up container combination that more easily rolls-up and unrolls. FIG. 8 shows one such exemplary embodiment wherein the flexible supportive base 5 comprises a front side material 5A and a back side material 5B, wherein the front side material 5A exhibits a greater attachment force to the viscoelastomeric thermoset overlay 3 as compared to the adhesive force between the back side material 5B and the overlay 3. FIG. 8 also shows that a perimeter portion of the back side material 5B is optionally folded over onto the peripheral edge portion of the front side material 5A, and the composite is thereafter held together via optional stitching SC. In such an exemplary embodiment, it can be desirable that each viscoelastomeric thermoset overlay 3 is disposed upon the base 5 such that the overlay 3 substantially only contacts the surface of the front side material 5A when in a laid-flat configuration.

In one exemplary embodiment (described further below), natural and synthetic leathers can also provide a suitable supportive base 5 which may be altered so as to provide two different surfaces having different attraction affinities towards the overlay 3. For example, the front side surface 5A of an unfinished or roughened leather (e.g., suede) can provide a front side 7 of the flexible supportive base 5 having a sufficient porosity and/or anchoring elements to embed and retain the viscoelastomeric thermoset overlay 3 thereto. In contrast, the opposing back side 9 of the base 5 can provide a back side surface 5B comprising a highly polished and smooth leather surface which will exhibit a lesser adhesive attraction towards the overlay 3 so as to permit an easier rolling and unrolling of the flexible container combination 1 without disengaging the overlay 3 from the front side 7, while still providing a sufficient adhesive attraction upon the interfacing surfaces of the back side 9 to maintain the flexible container combination 1 in a rolled up form. It should be understood that an adhesive attraction between the back side 9 of the supportive base 5 and the overlay 3 serves to assist in maintaining the rolled-up container combination 1 in a rolled-up state, thus eliminating the need for optional strings or other mechanical means to maintain the rolled-up container configuration, though the addition of such optional strings or other mechanical means would not depart from the scope of the invention (see e.g., FIGS. 5A-6B). Accordingly, such a flexible container combination 1 equipped with a flexible supportive base 5 wherein the back side 9 has a reduced adhesive affinity towards the overlay 3 as compared to the front side 7 upon which the overlay 3 is disposed thus provides an easy roll-up and unrolling version of the flexible container combination 1.

In another exemplary embodiment (described further below), another suitable flexible fabric base 5 includes a tightly-knitted cotton-based denim which permits thermosetting an overlay coating upon the front side 7 fabric surface 5A with uncured or partially cured thermosetting viscoelastomeric reaction media without allowing excessive seepage (e.g., no more than nominal or trace amounts) of the reaction media to migrate to the back side 9 fabric surface 5B of the flexible denim fabric base 5. As evident from the aforementioned, there exists numerous flexible bases 5, and techniques which can be applied, to coat or overlay the front side 7 of the flexible base 5 with the viscoelastomeric reaction product overlay 3.

Figure 7A:
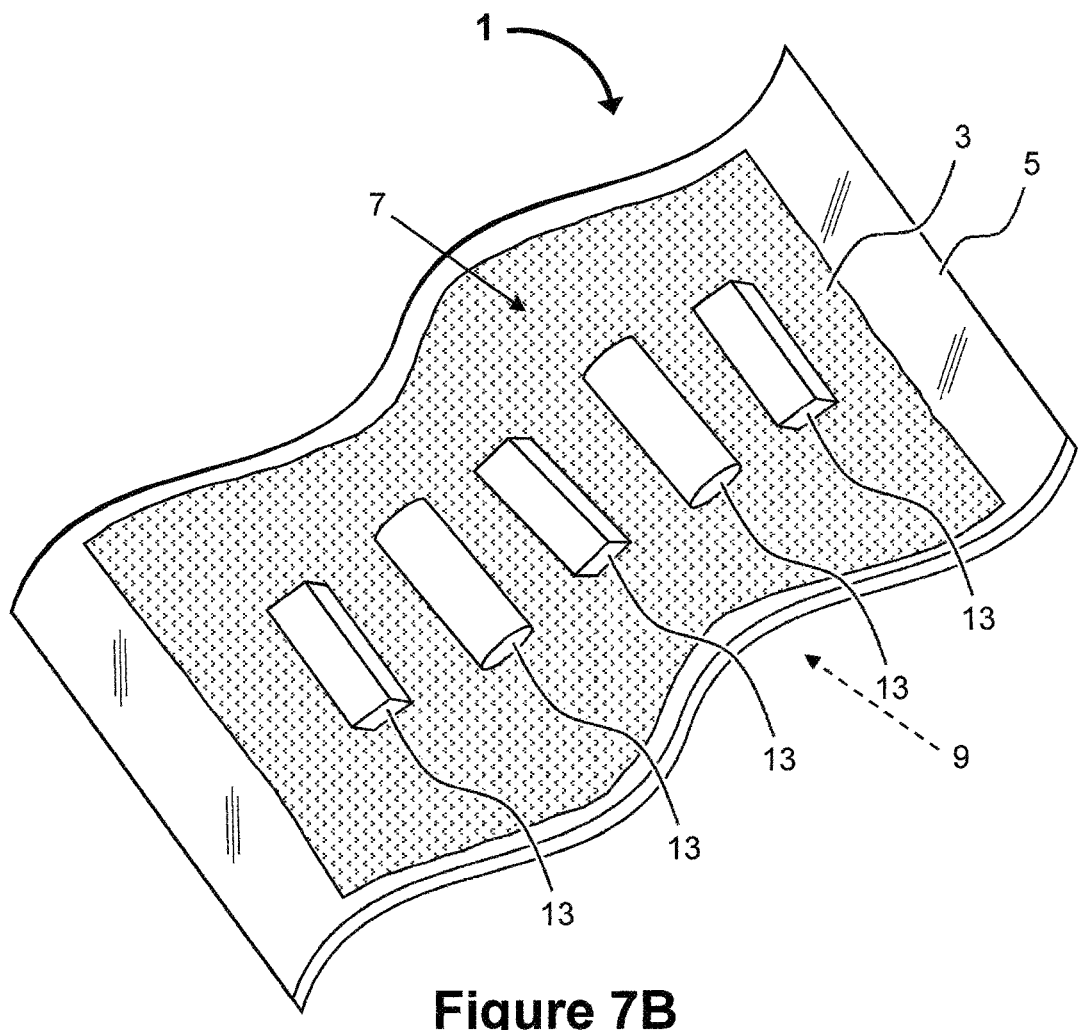
FIG. 7A is a perspective view showing an inventive flexible container combination of the present disclosure in the form of a transparent roll-up container in an open configuration comprising a transparent overlay at least partially disposed upon a transparent flexible supportive base substrate, and further comprising items protectively stowed upon the overlay.
Figure 7B:
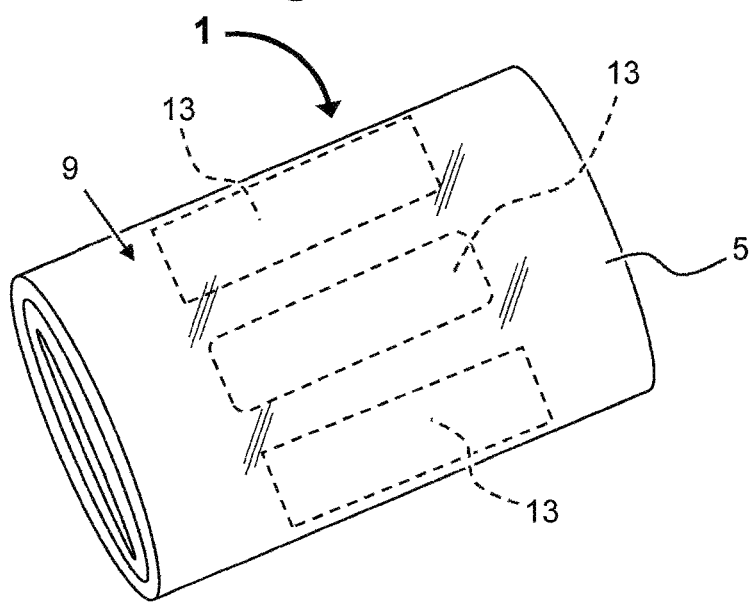
FIG. 7B is a perspective view showing the inventive transparent flexible container combination of FIG. 7A in a rolled-up configuration.

Referring now to FIGS. 7A-7B, in another exemplary embodiment, another suitable flexible base 5 includes a transparent material (e.g., transparent plastics, such as transparent polyethylene, transparent polypropylene, transparent polyurethane, etc.). Such transparent flexible bases 5 can be useful for forming a transparent flexible container combination 1. Accordingly, a transparent viscoelastomeric thermoset overlay 3 would desirably be disposed onto the front side 7 of the transparent flexible base 5. Ideally, in some such embodiments, an item 13 disposed within the transparent flexible container combination 1 could be visually discerned by a user (or another individual) having eyesight of 20/20 vision, even when the flexible container combination 1 is in a rolled-up, or otherwise folded, configuration. Such transparent flexible container combinations 1 can be useful for numerous venues (e.g., airports, athletic arenas, schools, etc.) where the items 13 must be identified, thus eliminating the inconvenience of opening-up the container and/or removing the items for inspection.

In some aspects, the flexible container combination 1 can comprise additional elements. For example, referring now to FIGS. 5A-5B, the flexible container combination 1 can comprise an optional strap 19 which can extend from the flexible supportive base 5, and which can be looped over the flexible container combination 1 when in a rolled-up form and/or used for transporting (e.g., carrying) the combination 1. Such optional strap 19 may be integral with the base 5, or may be disposed as a separate attachment to the base 5. In another example, referring now to FIGS. 6A-6B, the flexible container combination 1 can comprise optional enclosure panels 20 which extend from the flexible supportive base 5. Such optional enclosure panels 20 may be integral with the base 5, or may be disposed as separate attachments to the base 5. The optional enclosure panels 20 can serve to fully enclose the container combination 1 in its rolled up form. In addition, such enclosure panels 20 can comprise an optional fastener element 22 (e.g, hook-and-loop, adhesives, snaps, etc.) which can assist the enclosure panels 20 to remain in a closed configuration. Such optional strap 19 or optional enclosure panels 20 may be desirable when contained items 13 obstruct the adhesive interaction between the back side 9 uncoated flexible base surface 5B and the front side 7 coated flexible base surface 5A when in a rolled-up form, to facilitate the maintenance of the rolled up flexible container in a rolled up configuration, and/or for aesthetic purposes, for example.

Figure 3A:
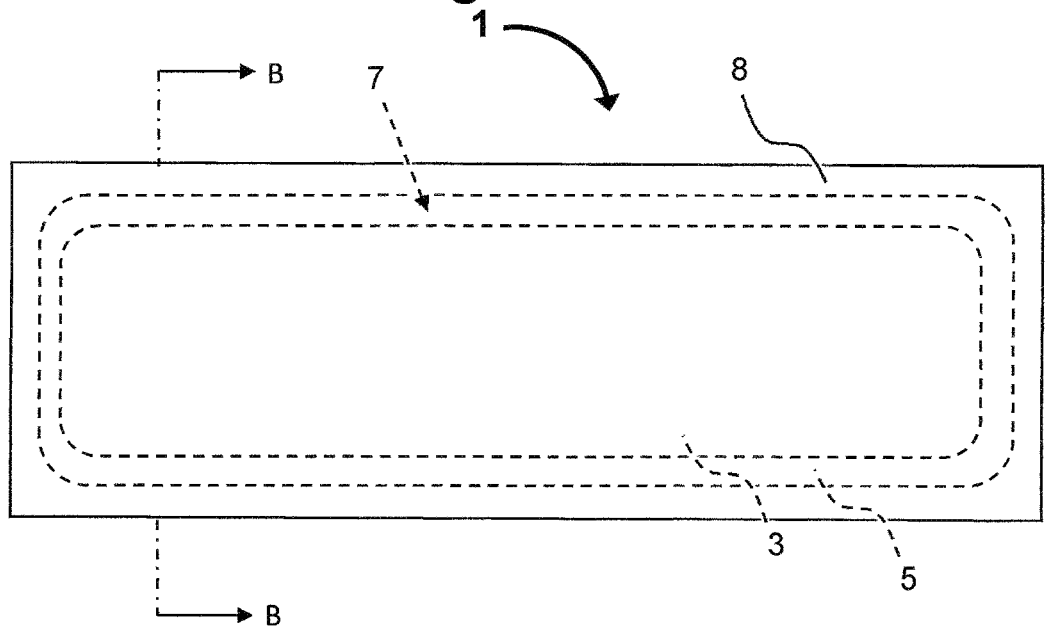
FIG. 3A is a perspective view showing an inventive flexible container combination of the present disclosure in the form of a roll-up container in an open configuration comprising an overlay at least partially disposed upon a flexible supportive base substrate, and further comprising a protective covering.
Figure 3B:
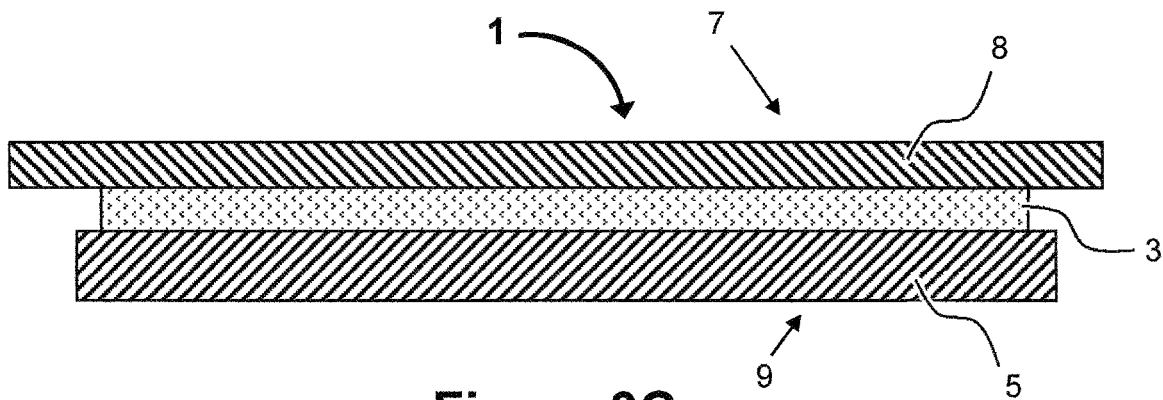
FIG. 3B is a cross-sectional view showing the inventive flexible container combination of FIG. 3A as taken along line B-B.
Figure 3C:
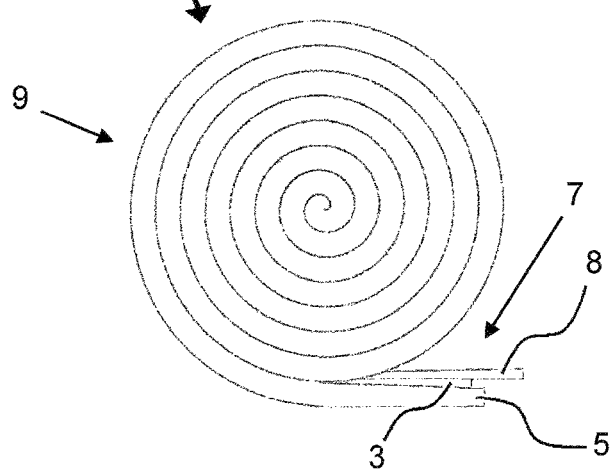
FIG. 3C is a side view showing the inventive flexible container combination of FIG. 3A in a rolled-up configuration.

With reference now to FIGS. 3A-3C, in some aspects, it can be desirable to include a protective covering 8 which can be at least partially disposed upon an exposed surface of the viscoelastomeric thermoset overlay 3. In general, a cured viscoelastomeric thermoset overlay 3 prepared from uncured or partially cured overlay reaction media reactants as referenced above may be readily adapted to adhere to a broad range of adhesively compatible flexible polymeric supportive bases 5, such as polyurethanes, polyethylene terephthalates, polyolefins (e.g., polyethylene and polypropylene), polyacrylates, polyesters, etc. However, as also referenced above, some materials (e.g., smooth PVC) may exhibit insufficient adhesive attraction properties (i.e., incompatible) to the viscoelastomeric thermoset overlay 3. For example, materials which have a lower adhesive affinity to the overlay 3 as compared to the overall attachment force of the overlay 3 to the front side 7 of the flexible supportive base 5 and/or which do not comprise suitable anchoring sites (i.e., such that the adhesive force between such materials is less than the attachment force between the overlay 3 and the front side 7 of the flexible supportive base 5) can be used with the invention to provide a protective covering 8 for exposed surfaces of the viscoelastomeric thermoset overlay 3. Such a protective covering 8 can be useful to prevent contamination of the overlay 3 from dust, lint, etc. and/or other accumulations which can adversely affect the adhesiveness of the overlay 3. In some aspects, such protective coverings 8 can also be useful as packaging materials for the invention, such as when shipping the flexible container combination 1 in commerce. Such protective coverings 8 can desirably be readily peeled away from the overlay 3 without disengaging the overlay 3 from the flexible supportive base 5, thus providing a clean, fully functional adhesive overlay 3. Examples of suitable protective coverings include, but are not limited to, polyvinylchloride (PVC) films and sheets, paraffin wax-coated paper, Teflon®, etc. In some aspects, a protective covering 8 can be utilized to separate the overlay 3 from the back side 9 of the flexible supportive base 5, such as when the flexible container combination 1 is in a rolled-up configuration, particularly when the flexible container combination 1 contains no stowed items 13 (e.g., when shipping the flexible container combination 1 in commerce).

It is believed that the unique embodiments of the present invention may also extend to other adhesives possessing similar adhesive and cohesive properties as possessed by the thermosetting reaction products and overlays 3 described herein. Although the aforementioned viscoelastomeric reaction media primarily centers about those viscoelastomers prepared from a unique thermosetting reaction media by incorporating a controlled straight chain linkage diol to cross-linkage triol ratio, with the isocyanate reactant, in the presence of a sufficient amount and type of plasticizer, so as to provide the desired adhesive and cohesive overlay 3, it is contemplated that this technology may also apply to other thermoset viscoelastomeric reaction products of a properly controlled cross-linked molecular structure separated by a proper amount of straight chain polyoxy linkages and polarity in the presence of sufficient polarized plasticizers, which yields a thermoset viscoelastomeric reaction product overlay 3 of comparably stable cohesiveness, adhesiveness and releasability properties. The adhesive strength, the cohesiveness, the thermoset reaction media attributes, the compositional uniformity, the releasability, the antipathogenic attributes, the flexibility, the cleansability, and a host of other salient attributes, possessed by the inventive viscoelastomeric thermoset overlay 3 uniquely and collectively distinguishes the flexible container combination 1 of this invention from conventional flexible containers.

The present invention may be better understood with reference to the following Examples.

EXAMPLES

Example 1

A viscoelastomeric thermoset reaction product adapted to provide a viscoelastomeric thermoset overlay 3 having exceptional onset fluidity, adhesiveness, cohesiveness and releasability efficacy was prepared by uniformly admixing together a two-part thermosetting reaction media mix comprised of:

|  | Percent by Weight: |
|---|---|
| Part A- Mix: Ingredients: | |
| Methylene diphenyl diisocyanate based glycol prepolymer (ELASTOCAST TQZP23 available from BASF Corporation) | 6.42% |
| Epoxidized soybean oil plasticizer | 26.9% |
| Dibutyl sebacate plasticizer | 8.97% |
| Part B- Mix: Ingredients: | |
| Polyether diol (ELASTOCAST C-4057 available from BASF Corporation) | 28.53% |
| Polyether triol (ELASTOCAST C-4018 available from BASF Corporation) | 27.72% |
| Catalyst (COSCAT 83 available from Vertellus Holdings LLC) | 0.16% |
| UV inhibitor (TINUVIN B75 available from BASF Corporation) | 1.30% |
| Total | 100% |

A 10 inch by 20-inch (25 cm×51 cm) leather substrate was provided as a flexible supportive base 5, wherein one side (i.e., the front side 7) consisted of a suede leather textured surface, and the opposing side (i.e., the back side 9) consisted of a polished leather textured surface. The leather substrate was selected because the polished leather side was characterized as having a lower adhesive attraction to a cured overlay 3 than its opposing suede leather surface.

The Part A-Mix ingredients and the Part B-Mix ingredients were each separately mixed. Then the Part A-Mix and Part B-Mix mixtures were combined and blended thoroughly to form a thermosetting reaction media. The resulting thermosetting reaction media of this Example 1 was then applied in liquid form to the suede leather front side 7 of the flexible supportive base 5. It was observed that the thermosetting reaction media partially penetrated into the porous subsurface regions of the suede leather surface, whereas the opposing polished side remained visibly free from any reaction media penetration. The applied thermosetting reaction media was then allowed to cure in situ at ambient temperature (i.e., about 21° C.) to form a viscoelastomeric thermoset overlay 3 that was tenaciously bonded to the suede leather side of the supportive base 5, thus resulting in a flexible leather container combination 1 of the invention herein. It was observed that the resulting flexible container combination 1 could be easily rolled and unrolled.

Figure 4A:
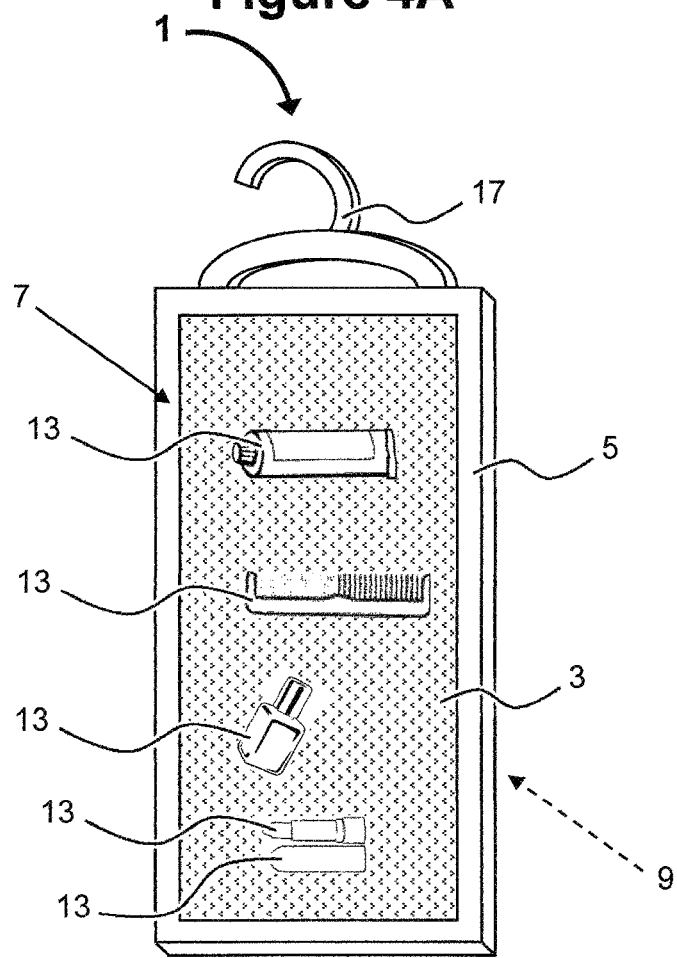
FIG. 4A is a perspective view showing an inventive flexible container combination of the present disclosure in the form of a hanging container in an open configuration comprising an overlay at least partially disposed upon a flexible supportive base substrate and having cosmetic items adhered to the overlay.
Figure 4B:
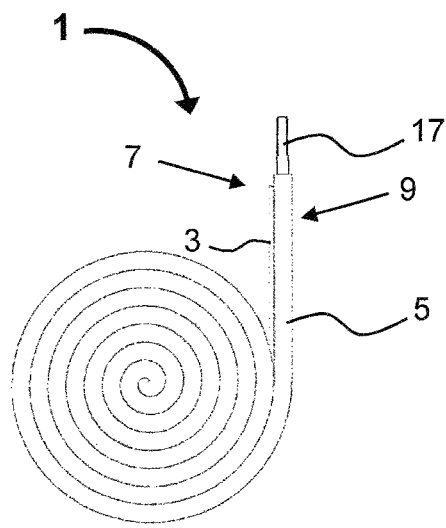
FIG. 4B is a side view showing the inventive flexible container combination of FIG. 4A in a rolled-up configuration.
Figure 5A:
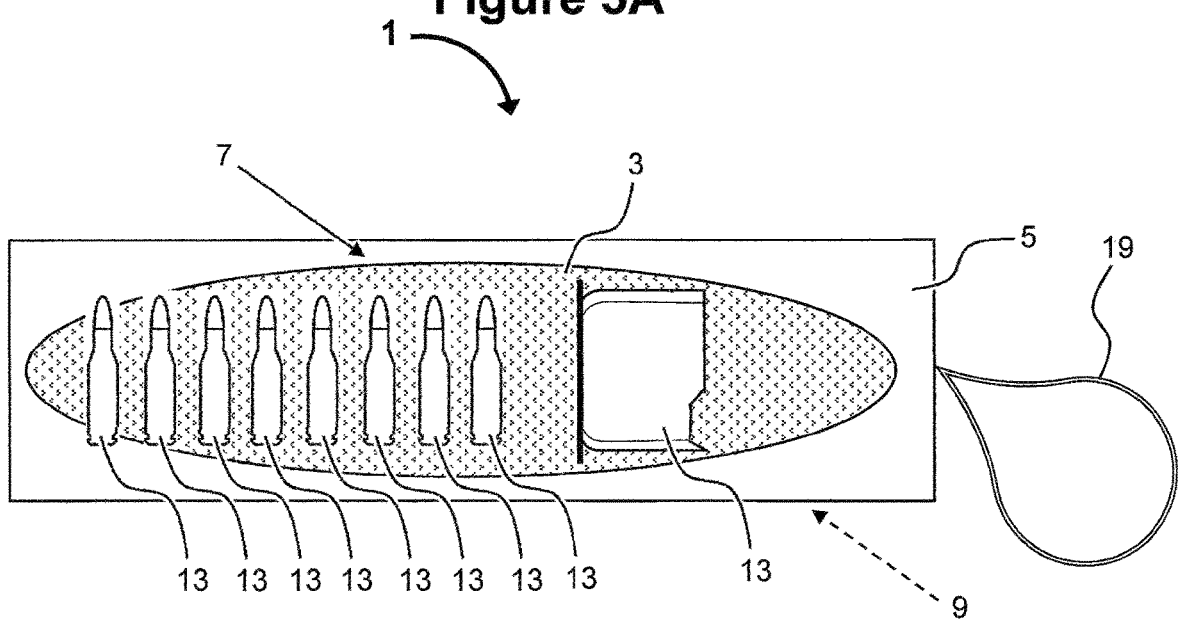
FIG. 5A is a top view showing an inventive flexible container combination of the present disclosure in an open configuration comprising an overlay at least partially disposed upon a flexible supportive base substrate, and further comprising an optional strap, and having ammunition and firearm accessories protectively stowed upon the overlay.
Figure 5B:
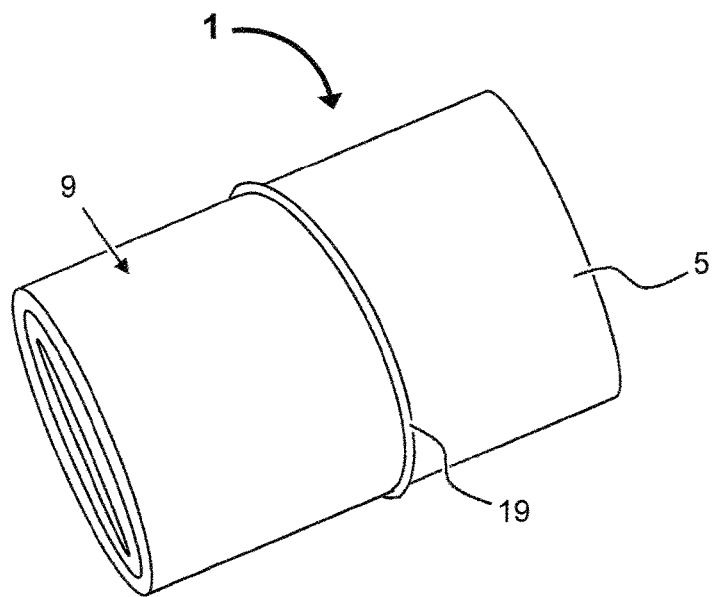
FIG. 5B is a perspective view showing the inventive flexible container combination of FIG. 5A in a rolled-up configuration.
Figure 6A:
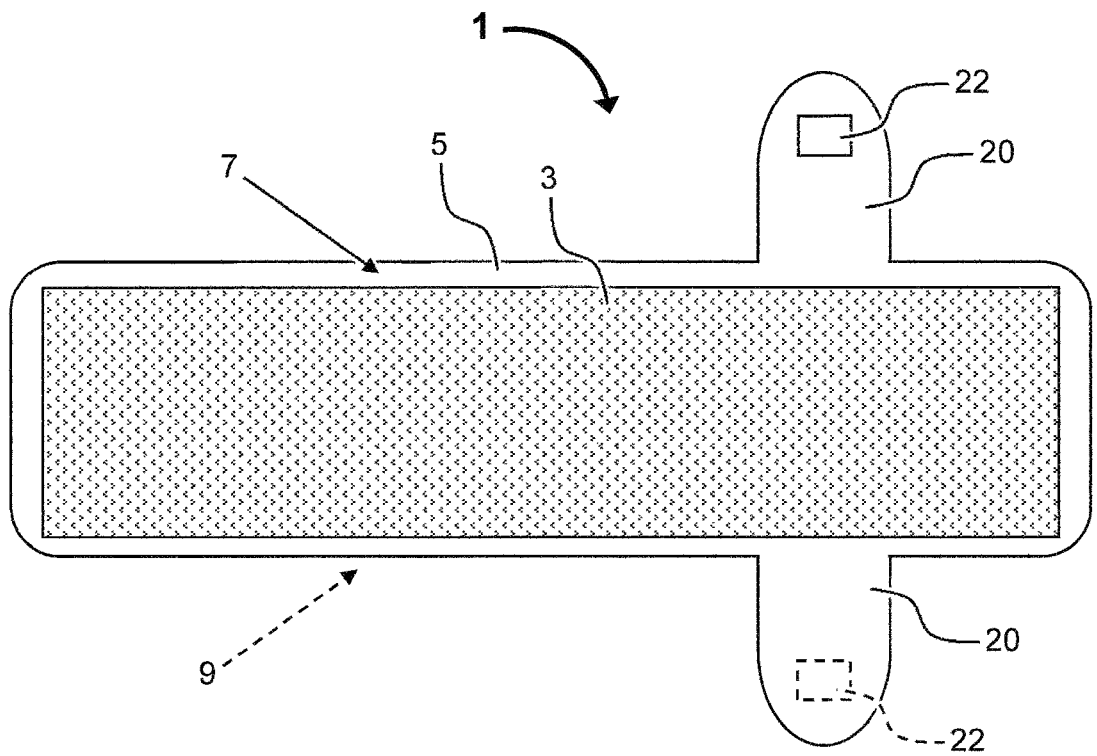
FIG. 6A is a perspective view of an inventive flexible container combination of the present disclosure in an open configuration comprising an overlay at least partially disposed upon a flexible supportive base substrate, and further comprising optional enclosure panels.
Figure 6B:
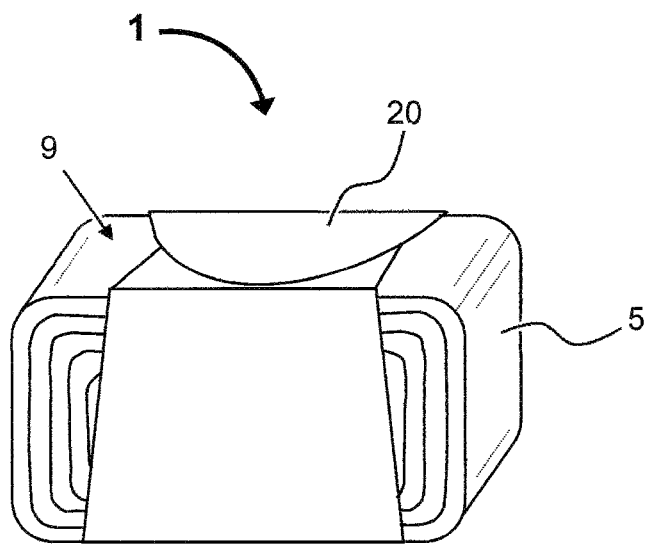
FIG. 6B is a perspective view showing the inventive flexible container combination of FIG. 6A in a closed configuration.

It was further observed that, since the adhesive attraction between the overlay 3 and the uncoated polished leather back side 9 of the flexible container combination 1 was lower than the overall attachment attraction between the overlay 3 and the suede leather front side 7, the flexible container combination 1, when rolled, provided an uncoated back side 9 leather surface which did not excessively stick to the abutting rolled up interfacing overlay 3, but also provided sufficient adhesiveness to maintain the rolled-up configuration of the flexible container combination 1, and furthermore did not separate the overlay 3 from the suede leather front side 7 when the flexible container combination 1 was unrolled. The resultant flexible container combination 1 provided an excellent roll-up container combination for a host of stowable objects, such as depicted by FIGS. 4A, 5A and 7A.

Example 2

A viscoelastomeric thermoset reaction product for use as a viscoelastomeric thermoset overlay 3 containing 45.84 wt % epoxidized soybean oil plasticizer was prepared by uniformly admixing together a two-part thermosetting reaction media mix comprised of

|  | Percent by Weight: |
|---|---|
| Part A- Mix: Ingredients: | |
| Methylene diphenyl diisocyanate based glycol prepolymer (ELASTOCAST TQZP23 available from BASF Corporation) | 5.56% |
| Epoxidized soybean oil plasticizer | 44.44% |
| Part B- Mix: Ingredients: | |
| Polyether diol (ELASTOCAST C-4057 available from BASF Corporation) | 28.0% |
| Polyether triol (ELASTOCAST C-4018 available from BASF Corporation) | 17.52% |
| Epoxidized soybean oil plasticizer | 1.40% |
| Catalyst (COSCAT 83 available from Vertellus Holdings LLC) | 0.52% |
| UV inhibitor (TINUVIN B75 available from BASF Corporation) | 1.12% |
| Colorant | 1.44% |
| Total | 100% |

Example 2a

The Part A-Mix ingredients and the Part B-Mix ingredients were each separately mixed. Then the Part A-Mix and Part B-Mix mixtures were combined and blended thoroughly to form a thermosetting reaction media. A 3 mm thick layer of the resulting thermosetting reaction media of this Example 2 was then applied to the front side of a flexible supportive base substrate comprised of a 0.3 mm thick high-density polypropylene film, and the applied thermosetting reaction media layer was allowed cure in situ at ambient temperature (i.e., about 21° C.) to provide a flexible container combination 1 comprising a viscoelastomeric thermoset overlay 3 bonded to a flexible supportive base 5.

Example 2b

A stand-alone viscoelastomeric thermoset overlay 3 was fabricated by applying a 10 mil (0.3 mm) thick layer of the resulting thermosetting reaction media of this Example 2 to a PVC sheet and was allowed to cure at ambient temperature (i.e., about 21° C.). The peelable viscoelastomeric thermoset overlay 3 was then used to convert a conventional (non-adhesive) roll-up container into a flexible container combination 1 of this invention by removing the viscoelastomeric thermoset overlay 3 from the PVC sheet and adhesively applying it to the front side 7 of the conventional container.

It was observed that the epoxidized soybean oil plasticizer content, along with the diol to triol ratio of this Example 2, appears to have significantly contributed to the bonding strength of the cured reaction media to a host of flexible supportive bases 5, especially when cured in situ as in Example 2a.

It was also observed that the overlay 3 derived from Example 2b may be transported in the channels of commerce as a stand-alone viscoelastomeric thermoset overlay 3, which can later be peeled away from the PVC sheet and then installed by the ultimate consumer to form a flexible container combination 1 of the invention herein.

Prefabricated viscoelastomeric thermoset overlays 3 such as formed in Example 2b would desirably be protected on both surfaces by a protective covering 8 (e.g., a PVC sheet). It was observed that such stand-alone overlays 3 can be most suitably formulated with about 40 percent to about 50 percent by weight epoxidized triglyceride plasticizer. It is believed that at epoxidized plasticizer levels below about 40 percent by weight, the peelablility factor may become more difficult.

Example 3

Example 3 utilized a similar Part A-Mix and Part B-Mix as in Example 1, except for increasing the epoxidized soybean oil plasticizer content and decreasing the dibutyl sebacate plasticizer content.

|  | Percent by Weight: |
|---|---|
| Part A- Mix: Ingredients: | |
| Methylene diphenyl diisocyanate based glycol prepolymer (ELASTOCAST TQZP23 available from BASF Corporation) | 6.42% |
| Epoxidized soybean oil plasticizer | 30.78% |
| Dibutyl sebacate plasticizer | 5.09% |

-continued

| | Percent by Weight: |
|---|---|
| Part B- Mix: Ingredients: | |
| Polyether diol (ELASTOCAST C-4057 available from BASF Corporation) | 28.53% |
| Polyether triol (ELASTOCAST C-4018 available from BASF Corporation) | 27.72% |
| Catalyst (COSCAT 83 available from Vertellus Holdings LLC) | 0.16% |
| UV inhibitor (TINUVIN B75 available from BASF Corporation) | 1.30% |
| Total | 100% |

The Part A-Mix ingredients and the Part B-Mix ingredients were each separately mixed. Then the Part A-Mix and Part B-Mix mixtures were combined and blended thoroughly to form a thermosetting reaction media. A layer measuring about 1 mm thick of the resulting thermosetting reaction media of this Example 3 was then applied in liquid form to the front side of a 0.5 mm thick tightly woven denim cloth measuring about 20 cm by about 46 cm to provide a roll-up flexible container combination 1 of the invention herein. Particular precautions were taken to prevent the liquid reaction media from penetrating all the way through to the opposing back side of the denim cloth (e.g., increasing the epoxidized soybean oil plasticizer content and decreasing the viscosity-reducing dibutyl sebacate plasticizer content). The applied thermosetting reaction media was then allowed to cure in situ at ambient temperature (i.e., about 21° C.) to provide a flexible container combination 1 possessing excellent roll-up and unrolling attributes, with the viscoelastomeric thermoset overlay 3 being securely and firmly bonded to the front side 7 of the denim cloth base 5. The overlay 3 possessed exceptional adhesive and cohesive release properties. Similar overlaying techniques utilizing a host of other woven fabrics may also be effectively used to prepare the flexible container combinations 1 herein. It was observed that in applying the uncured reaction media to the denim cloth base 5, the most appropriate application viscosity can be controlled by altering the weight ratios of epoxidized soybean oil plasticizer to dibutyl sebacate plasticizer.

Example 4

A viscoelastomer thermoset overlay was prepared from a thermosetting reaction media comprised of:

| | Percent by Weight: |
|---|---|
| Part A-Mix: Ingredients: | |
| Methylene diphenyl diisocyanate based glycol prepolymer (ELASTOCAST TQZP23 available from BASF Corporation) | 6.51% |
| Epoxidized soybean oil plasticizer | 26.73% |
| Dibutyl sebacate plasticizer | 8.91% |
| Part B-Mix: Ingredients: | |
| Polyether triol (ELASTOCAST C-4018 available from BASF Corporation) | 30.79% |
| Polyether diol (ELASTOCAST C-4057 by BASF Corporation) | 25.11% |
| Catalyst (COSCAT 83 available from Vertellus Holdings LLC) | 0.16% |

-continued

| | Percent by Weight: |
|---|---|
| UV inhibitor (TINUVIN B75 available from BASF Corporation) | 1.30% |
| Colorant | 0.49% |
| Total | 100% |

The Part A-Mix ingredients and the Part B-Mix ingredients were each separately mixed. Then the Part A-Mix and Part B-Mix mixtures were combined and blended thoroughly to form a thermosetting reaction media. A multilayered flexible base measuring about 20 cm by about 46 cm was provided comprising a 0.5 mm thick denim fabric to which a backing layer comprised of 35 wt % polyvinyl chloride and 65 wt % polyether (WUJI gold foil leather, available from JoAnn Fabrics) was sewn. A layer measuring about 1 mm thick of the resulting thermosetting reaction media of this Example 4 was then applied to the denim fabric layer of the base. The uncured thermosetting reaction media was applied as a uniform overlay penetrating and anchoring into the denim fabric. The 65% polyester/35% PVC backing served to prevent the thermosetting reaction media from penetrating through to the back side of the base. The applied thermosetting reaction media was then allowed to cure in situ at ambient temperature (i.e., about 21° C.).

Upon curing, the resulting viscoelastomeric thermoset overlay 3 exhibited excellent cohesive and adhesive properties. Several items were then placed onto the viscoelastomeric thermoset overlay 3, and it was observed that the stowed items 13 exhibited tenacious adherence to the overlay 3. It was also observed that, when removed from the viscoelastomeric thermoset overlay 3, the separated items were visually free from any overlay 3 residue. Although the removal of the items 13 from the inventive combination 1 caused initial distortion of the overlay 3, the overlay 3 readily returned to its innate form after separation of the items 13 therefrom. It was also observed that upon removal of the items 13 from the combination 1, the overlay 3 did not separate from the denim fabric of the base 5.

It was further observed that since the thermosetting reaction media did not permeate through the base 5 to the 65% polyester/35% PVC back side 9 surface 5B, the flexible container combination could be easily rolled into a rolled-up container configuration, and then easily unrolled into a flat configuration, as desired. It was also observed that the overlay 3 provided sufficient adhesion to maintain the flexible container combination in a rolled-up configuration. If desired, strings and/or end flaps could optionally be added to the flexible container combination 1 to enclose the flexible container in a rolled-up configuration, but they were not needed. The use of such a flexible backing material barrier to limit reaction media penetration onto the back side 9 of the flexible support base 5 can be applied to a host of flexible bases. Alternatively, the type of fabric or flexible support, in combination with a thermosetting reaction media of an appropriate viscosity and curing time, can be effectively utilized to control the depth of fabric or other flexible support penetration.

It was also observed that the flexible container combination 1 exhibited antipathogenic properties. Such antipathogenic properties can help to maintain sanitary conditions.

In addition, it was also observed that, should a reduction in adhesion occur (e.g., from dust accumulation), the original adhesiveness could be readily restored by utilizing simple hand washing under a faucet using common dish detergent.

It will be appreciated that details of the foregoing examples, given for purposes of illustration, are not to be construed as limiting the scope of the present invention. Although only a few exemplary embodiments of the present invention have been described in detail above, persons having skill in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of the present invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A flexible container combination comprising a flexible supportive base having a front side and a back side, and an adhesive and cohesive viscoelastomeric thermoset overlay disposed upon the front side of the flexible supportive base.

2. The flexible container combination of claim 1, wherein the flexible container combination is in the form of a roll-up container; and wherein an overall attachment force of the viscoelastomeric thermoset overlay to the front side of the flexible supportive base is greater than an adhesive force of the viscoelastomeric thermoset overlay to the back side of the flexible supportive base.

3. The flexible container combination of claim 1, wherein the flexible container combination is in the form of a bag.

4. The flexible container combination of claim 1, wherein the flexible container combination is in the form of a hanging container.

5. The flexible container combination of claim 1, wherein at least one of the viscoelastomeric thermoset overlay or flexible supportive base is transparent.

6. The flexible container combination of claim 1, wherein the viscoelastomeric thermoset overlay has a thickness of about 0.5 mm to about 10 mm.

7. The flexible container combination of claim 1, wherein the front side of the flexible supportive base is at least partially impregnated with the viscoelastomeric thermoset overlay, and wherein the back side of the flexible supportive base is substantially free of the viscoelastomeric thermoset overlay.

8. The flexible container combination of claim 1, wherein the viscoelastomeric thermoset overlay comprises:
 a) about 1 wt % to about 10 wt % isocyanate prepolymer;
 b) about 35 wt % to about 65 wt % polyols comprising straight chain linking diols and cross-linking triols;
 c) about 10 wt % to about 50 wt % epoxidized triglyceride plasticizer; and
 d) 0 wt % to about 40 wt % ester plasticizer;
 wherein the diols and triols each have repetitive ether groupings.

9. The flexible container combination of claim 8, wherein the epoxidized triglyceride plasticizer and the ester plasticizer are uniformly dispersed throughout the viscoelastomeric thermoset overlay.

10. The flexible container combination of claim 8, wherein the viscoelastomeric thermoset overlay has been bonded to the flexible supportive base via in situ curing.

11. The flexible container combination of claim 8, wherein the viscoelastomeric thermoset overlay further comprises an epoxidized triglyceride plasticizer to ester plasticizer weight ratio of about 1:0 to about 6:1.

12. The flexible container combination of claim 8, wherein the ester plasticizer is selected from the group consisting of sebacates, dipates, glutarates, dibenzoates, phthalates, terephthalates, azelates, and combinations thereof.

13. The flexible container combination of claim 8, wherein the ester plasticizer has a molecular weight of less than about 750.

14. The flexible container combination of claim 8, wherein the ester plasticizer has a dipole moment of at least about 1.5 D.

15. The flexible container combination of claim 8, wherein the ester plasticizer comprises dibutyl sebacate in an amount of about 2 wt % to about 20 wt %.

16. The flexible container combination of claim 8, wherein the flexible container combination is transparent.

17. The flexible container combination of claim 8, wherein the viscoelastomeric thermoset overlay comprises:
 a) about 3 wt % to about 8 wt % diisocyanate prepolymer;
 b) about 10 wt % to about 35 wt % polyether diol as the straight chain linking diols;
 c) about 25 wt % to about 35 wt % polyether triol as the cross-linking triols;
 d) about 25 wt % to about 45 wt % epoxidized vegetable oil plasticizer; and
 e) 0 wt % to about 40 wt % ester plasticizer.

18. The flexible container combination of claim 17, wherein the viscoelastomeric thermoset overlay further comprises a polyether diol to polyether triol weight ratio of about 3:1 to about 1:3.

19. The flexible container combination of claim 17, wherein the polyether diol and the polyether triol each comprise a polyoxyalkylene grouping selected from the group consisting of polyoxyethylene and polyoxypropylene; and wherein the polyether diol and the polyether triol each have a molecular weight of about 2,000 to about 10,000.

20. The flexible container combination of claim 17, wherein the viscoelastomeric thermoset overlay comprises a sufficient adhesiveness to retain an item disposed thereon against displacement via gravity, and further to provide a sufficient cohesiveness to retain structural integrity of the viscoelastomeric thermoset overlay upon removal of the item via a separation force by a user.

21. The flexible container combination of claim 17, wherein the viscoelastomeric thermoset overlay comprises:
 a) about 4 wt % to about 7 wt % diisocyanate prepolymer;
 b) about 10 wt % to about 20 wt % polyether diol having a molecular weight of about 2,000 to about 6,000;
 c) about 25 wt % to about 35 wt % polyether triol having a molecular weight of about 3,000 to about 7,000;
 d) about 25 wt % to about 45 wt % percent epoxidized soybean oil plasticizer; and
 e) 0 wt % to about 40 wt % ester plasticizer having a molecular weight of less than about 750;

wherein the viscoelastomeric thermoset overlay further comprises a polyether diol to polyether triol weight ratio of about 13:7 to about 7:13;

wherein the viscoelastomeric thermoset overlay further comprises an epoxidized soy bean oil plasticizer to ester plasticizer weight ratio of about 1:0 to about 6:1; and wherein a reaction to form the viscoelastomeric thermoset overlay is carried out in the presence of a catalytic amount of a catalyst.

22. A flexible container combination comprising:
a) a flexible supportive base having a front side and a back side; and
b) an adhesive and cohesive viscoelastomeric thermoset overlay disposed upon the front side of the flexible supportive base;
wherein the viscoelastomeric thermoset overlay comprises a sufficient adhesive attraction to immobilize a stowed item placed in adhesive contact with the viscoelastomeric thermoset overlay; and
wherein the viscoelastomeric thermoset overlay further comprises a sufficient cohesive releasability to detach the stowed item upon an application of a removing force sufficient to overcome the adhesive attraction.

23. The flexible container combination of claim 22, wherein the flexible container combination is transparent.

24. A method for preparing a flexible container combination comprising:
a) providing a flexible supportive base having a front side and a back side, wherein the flexible supportive base is of a sufficient size and structural integrity to support a stowable item; and
b) overlaying the front side of the flexible supportive base with a thermoset viscoelastomeric reaction product to form a viscoelastomeric thermoset overlay disposed thereupon;
wherein the viscoelastomeric thermoset overlay is bonded to the flexible supportive base by a thermoset bonding of the thermoset viscoelastomeric reaction product to the front side of the flexible supportive base or by an adhesive bonding of the viscoelastomeric thermoset overlay to the front side of the flexible supportive base;
wherein the viscoelastomeric thermoset overlay possesses adhesive, cohesive and releasability properties sufficient to retain a stowable item at a stabilized stowable position to form a stowed item, and to release the stowed item by application of a detachment force sufficient to overcome an adhesive attraction between the stowed item and the viscoelastomeric thermoset overlay to form a removed item; and
wherein the removed item exhibits no more than a nominal amount of a polymeric residue from the viscoelastomeric thermoset overlay.

25. The method of claim 24, wherein the overlaying comprises disposing a reaction media which forms the thermoset viscoelastomeric reaction product onto the front side of the flexible supportive base and then curing the reaction media in situ.

26. The method of claim 24, wherein the overlaying comprises adhesively disposing a cured layer of the thermoset viscoelastomeric reaction product upon the front side of the flexible supportive base; and wherein the layer has a thickness of about 0.5 mm to about 10 mm.

27. The method of claim 24, wherein at least one of the viscoelastomeric thermoset overlay or flexible supportive base is transparent.

28. The method of claim 24, wherein the viscoelastomeric thermoset overlay is derived from a thermosetting of a reaction media comprising:
a) about 1 wt % to about 10 wt % diisocyanate prepolymer;
b) about 35 wt % to about 65 wt % polyols comprising straight chain linking diols and cross-linking triols; and
c) about 10 wt % to about 55 wt % plasticizer comprising about 10 wt % to about 50 wt % epoxidized triglyceride plasticizer and 0 wt % to about 40 wt % ester plasticizer;
wherein the diols and triols each have repetitive ether groupings.

29. The method of claim 28, wherein the reaction media further comprises an epoxidized triglyceride plasticizer to ester plasticizer weight ratio of about 1:0 to about 6:1.

30. The method of claim 28, wherein the ester plasticizer has a molecular weight of less than about 750.

31. The method of claim 28, wherein the ester plasticizer has a dipole moment of at least about 1.5 D.

32. The method of claim 28, wherein the ester plasticizer is selected from the group consisting of sebacates, dipates, glutarates, dibenzoates, phthalates, terephthalates, azelates, and combinations thereof.

33. The method of claim 28, wherein the reaction media comprises:
a) about 3 wt % to about 8 wt % diisocyanate prepolymer;
b) about 10 wt % to about 35 wt % polyether diol as the straight chain linking diol;
c) about 25 wt % to about 35 wt % polyether triol as the cross-linking triol; and
d) about 20 wt % to about 50 wt % plasticizer comprising about 10 wt % to about 45 wt % epoxidized vegetable oil plasticizer and 0 wt % to about 40 wt % dibutyl sebacate plasticizer;
wherein the polyether diol and the polyether triol each have a molecular weight ranging from about 2,000 to about 10,000; and
wherein the plasticizer is uniformly and cohesively dispersed throughout the reaction media.

34. The method of claim 33, wherein the polyether diol and the polyether triol each comprise a polyoxyalkylene grouping selected from the group consisting of polyoxyethylene and polyoxypropylene.

* * * * *